(12) United States Patent
DeWitt et al.

(10) Patent No.: US 11,773,080 B2
(45) Date of Patent: Oct. 3, 2023

(54) DEUTERIUM-ENRICHED ISOINDOLINONYL-AZEPANEDIONES AND RELATED COMPOUNDS AND METHODS OF TREATING MEDICAL DISORDERS USING SAME

(71) Applicant: Salarius Pharmaceuticals, Inc., Houston, TX (US)

(72) Inventors: Sheila DeWitt, Auburn, NH (US); Vincent Jacques, Somerville, MA (US)

(73) Assignee: Salarius Pharmaceuticals, Inc., Houston, TX (US)

( * ) Notice: Subject to any disclaimer, the term of this patent is extended or adjusted under 35 U.S.C. 154(b) by 189 days.

(21) Appl. No.: 16/956,741

(22) PCT Filed: Dec. 21, 2018

(86) PCT No.: PCT/US2018/067199
§ 371 (c)(1),
(2) Date: Jun. 22, 2020

(87) PCT Pub. No.: WO2019/126704
PCT Pub. Date: Jun. 27, 2019

(65) Prior Publication Data
US 2021/0340125 A1 Nov. 4, 2021

Related U.S. Application Data

(60) Provisional application No. 62/609,446, filed on Dec. 22, 2017.

(51) Int. Cl.
*C07D 403/04* (2006.01)
*C07B 59/00* (2006.01)

(52) U.S. Cl.
CPC .......... *C07D 403/04* (2013.01); *C07B 59/002* (2013.01); *C07B 2200/05* (2013.01)

(58) Field of Classification Search
CPC ............................. C07D 403/04; A61K 31/55
USPC ..................................... 540/524; 514/211.03
See application file for complete search history.

(56) References Cited

U.S. PATENT DOCUMENTS

| | | |
|---|---|---|
| 9,090,585 B2 | 7/2015 | DeWitt |
| 9,290,475 B2 | 3/2016 | DeWitt |
| 9,540,340 B2 | 1/2017 | DeWitt |

FOREIGN PATENT DOCUMENTS

WO 2016191178 A1 12/2016

OTHER PUBLICATIONS

International Search Report for PCT/US2018/067199 dated Apr. 1, 2019.

*Primary Examiner* — Jeffrey H Murray
(74) *Attorney, Agent, or Firm* — Goodwin Procter LLP

(57) ABSTRACT

The invention provides deuterium-enriched isoindolinonyl-azepanediones, deuterium-enriched oxoquinazolin-3(4H)-yl-azepanediones, related compounds, pharmaceutical compositions, and methods of using such compounds and pharmaceutical compositions to treat cancer, angiogenesis disorders, immune disorders, and other medical disorders.

6 Claims, No Drawings

DEUTERIUM-ENRICHED ISOINDOLINONYL-AZEPANEDIONES AND RELATED COMPOUNDS AND METHODS OF TREATING MEDICAL DISORDERS USING SAME

CROSS-REFERENCE TO RELATED APPLICATION

This application is the national stage of International (PCT) Patent Application Serial No. PCT/US2018/067199, filed Dec. 21, 2018 which claims priority to U.S. Provisional Application No. 62/609,446, filed Dec. 22, 2017, which is incorporated herein by reference in its entirety.

FIELD OF THE INVENTION

The invention provides deuterium-enriched isoindolinonyl-azepanediones, deuterium-enriched oxoquinazolin-3(4H)-yl-azepanediones, related compounds, pharmaceutical compositions, and methods of using such compounds and pharmaceutical compositions to treat cancer, angiogenesis disorders, immune disorders, and other medical disorders.

BACKGROUND

Cancer remains a substantial challenge to human health. Cancer is frequently characterized by an increase in the number of abnormal cells derived from a given normal tissue. Exemplary cancers that impact a substantial percentage of the patient population include, for example, cancer of the lung, colon, rectum, prostate, breast, and blood. The incidence of cancer continues to increase as the general population ages, new cancers develop, and susceptible populations (e.g., people infected with AIDS) grow. Notwithstanding the significant need for cancer therapy, options for the treatment of cancer are limited. For example, in the case of blood cancers (e.g., multiple myeloma), few treatment options are available, especially when conventional chemotherapy fails and bone marrow transplantation is not an option. A substantial demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. One mechanism is the secretion by tumor cells of cytokines with angiogenic properties. Examples of these cytokines include acidic and basic fibroblastic growth factor (bFGF), angiogenin, vascular endothelial growth factor (VEGF), and TNF-α. Alternatively, tumor cells can release angiogenic peptides through the production of proteases and the subsequent breakdown of the extracellular matrix where some cytokines are stored. Angiogenesis can also be induced indirectly through the recruitment of inflammatory cells (particularly macrophages) and the subsequent release of angiogenic cytokines (e.g., TNF-α, bFGF). A variety of disorders are also associated with undesired angiogenesis. Thus, a need exists for improved methods and agents for inhibiting angiogenesis.

The present invention addresses these unmet needs and provides additional advantages.

SUMMARY

The invention provides deuterium-enriched isoindolinonyl-azepanediones, deuterium-enriched oxoquinazolin-3(4H)-yl-azepanediones, related compounds, pharmaceutical compositions, and methods of treating medical disorders using a deuterium-enriched isoindolinonyl-azepanedione, a deuterium-enriched oxoquinazolin-3(4H)-yl-azepanedione, or related compound described herein. Certain deuterium-enriched isoindolinonyl-azepanediones, deuterium-enriched oxoquinazolin-3(4H)-yl-azepanediones, and related compounds contain deuterium enrichment at the chiral center of the azepane-2,7-dione group and optionally at other locations of the compounds. Further, the deuterium-enriched isoindolinonyl-azepanediones, deuterium-enriched oxoquinazolin-3(4H)-yl-azepanediones, and related compounds may be provided in enantiomerically pure form. These features are contemplated to provide therapeutic agents with improved properties.

Accordingly, one aspect of the invention provides a deuterium-enriched compound of Formula I:

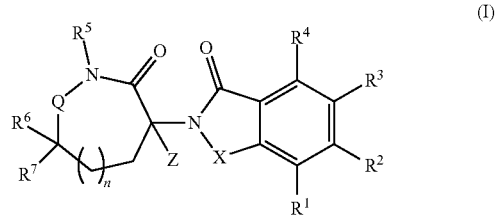

(I)

or a pharmaceutically acceptable salt, solvate, or stereoisomer thereof, wherein the variables are as defined in the detailed description; and any hydrogen atom may be optionally replaced with D.

Another aspect of the invention provides a deuterium-enriched compound of Formula

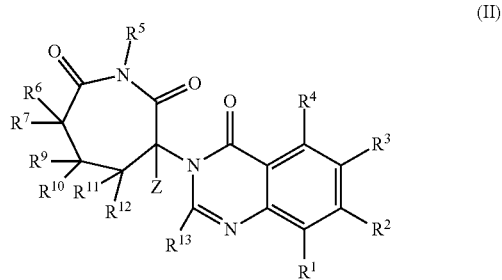

(II)

or a pharmaceutically acceptable salt, solvate, or stereoisomer thereof; wherein the variables are as defined in the detailed description; and any hydrogen atom may be optionally replaced with D.

Another aspect of the invention provides a deuterium-enriched compound of Formula II-X:

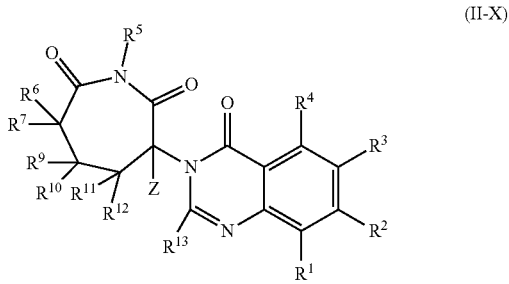

(II-X)

or a pharmaceutically acceptable, solvate, or stereoisomer thereof; wherein the variables are as defined in the detailed description.

In certain embodiments, the deuterium-enriched compound is a compound of Formula II-Y represented by

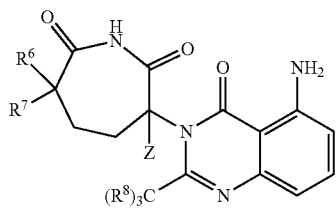
(II-Y)

or a pharmaceutically acceptable salt thereof; wherein Z is H or D, provided that the abundance of deuterium in Z is at least 30%; $R^6$, $R^7$, and $R^8$ are independently H or D; and any hydrogen atom may be optionally replaced with D.

In certain embodiments, the deuterium-enriched compound is a compound of Formula III represented by:

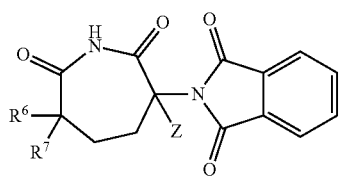
(III)

or a pharmaceutically acceptable salt, solvate, or stereoisomer thereof; wherein Z is H or D, provided that the abundance of deuterium in Z is at least 30%; $R^6$ and $R^7$ are independently H or D; and any hydrogen atom may be optionally replaced with D.

In certain embodiments, the deuterium-enriched compound is a compound of Formula IV represented by:

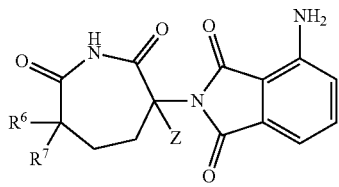
(IV)

or a pharmaceutically acceptable salt, solvate, or stereoisomer thereof; wherein Z is H or D, provided that the abundance of deuterium in Z is at least 30%; $R^6$ and $R^7$ are independently H or D; and any hydrogen atom may be optionally replaced with D.

In certain embodiments, the deuterium-enriched compound is a compound of Formula V represented by:

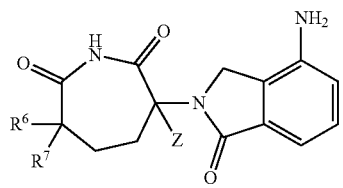
(V)

or a pharmaceutically acceptable salt, solvate, or stereoisomer thereof; wherein Z is H or D, provided that the abundance of deuterium in Z is at least 30%; $R^6$ and $R^7$ are independently H or D; and any hydrogen atom may be optionally replaced with D.

In certain embodiments, the deuterium-enriched compound is a compound of Formula VI represented by:

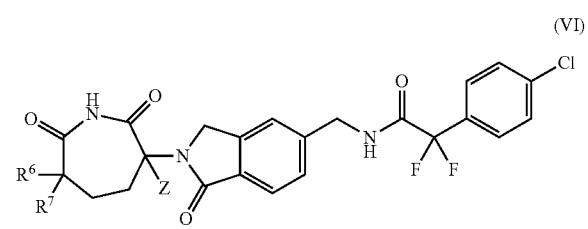
(VI)

or a pharmaceutically acceptable salt, solvate, or stereoisomer thereof; wherein Z is H or D, provided that the abundance of deuterium in Z is at least 30%; $R^6$ and $R^7$ are independently H or D; and any hydrogen atom may be optionally replaced with D.

Another aspect of the invention provides a pharmaceutical composition comprising a deuterium-enriched compound described herein (e.g., a deuterium-enriched isoindolinonyl-azepanedione, a deuterium-enriched oxoquinazolin-3(4H)-yl-azepanedione, or a related compound) and a pharmaceutically acceptable carrier.

Another aspect of the invention provides a method of treating a medical disorder described herein, such as a disorder selected from the group consisting of cancer, an immune disorder, and an inflammatory disorder. The method comprises administering to a patient in need thereof a therapeutically effective amount of a deuterium-enriched compound described herein (e.g., a deuterium-enriched isoindolinonyl-azepanedione, a deuterium-enriched oxoquinazolin-3(4H)-yl-azepanedione, or a related compound; such as a deuterium-enriched compound of Formula I, II, III, IV, V, or VI), to treat the disorder.

DETAILED DESCRIPTION

The invention provides deuterium-enriched isoindolinonyl-azepanediones, deuterium-enriched oxoquinazolin-3(4H)-yl-azepanediones, related compounds, pharmaceutical compositions, and methods of treating medical disorders using a deuterium-enriched isoindolinonyl-azepanedione, a deuterium-enriched oxoquinazolin-3(4H)-yl-azepanedione, or related compound described herein. Certain deuterium-enriched isoindolinonyl-azepanediones, deuterium-enriched oxoquinazolin-3(4H)-yl-azepanediones, and related compounds contain deuterium enrichment at the chiral center of the azepane-2,7-dione group and optionally at other locations of the compounds. Deuterium enrichment at the chiral center may reduce the rate at which the two enantiomers of the azepane-2,7-dione group may interconvert. Further, deuterium-enriched isoindolinonyl-azepanediones, deuterium-enriched oxoquinazolin-3(4H)-yl-azepanediones, and related compounds may be provided in enantiomerically pure form. These features are contemplated to provide therapeutic agents with improved properties.

Deuterium-enriched refers to the feature that the compound has a quantity of deuterium that is greater than in naturally occurring compounds or synthetic compounds prepared from substrates having the naturally occurring distribution of isotopes. The threshold amount of deuterium enrichment is specified in certain instances in this disclosure, and all percentages given for the amount of deuterium present are mole percentages.

Deuterium ($^2$H) is a stable, non-radioactive isotope of $^1$H hydrogen and has an atomic weight of 2.014. Hydrogen naturally occurs as a mixture of the isotopes $^1$H hydrogen (i.e., protium), deuterium ($^2$H), and tritium ($^3$H). The natural abundance of deuterium is 0.015%. One of ordinary skill in the art recognizes that in all chemical compounds with an H atom, the H atom actually represents a mixture of $^1$H hydrogen, deuterium ($^2$H), and tritium ($^3$H), where about 0.015% is deuterium. Thus, compounds with a level of deuterium that has been enriched to be greater than its natural abundance of 0.015% are considered unnatural and, as a result, novel over their non-enriched counterparts.

Exemplary compositions and methods of the present invention are described in more detail in the following sections: I. Deuterium-enriched Isoindolinonyl-azepanediones, Deuterium-enriched Oxoquinazolin-3(4H)-yl-azepanediones, and Related Compounds; II. Therapeutic Applications; III. Dosing Considerations and Combination Therapy, and IV. Pharmaceutical Compositions. Aspects of the invention described in one particular section are not to be limited to any particular section.

I. Deuterium-Enriched Isoindolinonyl-Azepanediones, Deuterium-Enriched Oxoquinazolin-3(4H)-Yl-Azepanediones, and Related Compounds One aspect of the invention provides deuterium-enriched compounds. Such deuterium-enriched compounds may be used in the therapeutic methods and pharmaceutical compositions described herein. As explained above, the deuterium-enriched isoindolinonyl-azepanediones, deuterium-enriched oxoquinazolin-3(4H)-yl-azepanediones, and related compounds described herein contain deuterium enrichment at the chiral center of the azepane-2,7-dione group. Deuterium enrichment at the chiral center may reduce the rate at which the two enantiomers of the azepane-2,7-dione group may interconvert.

Accordingly, one aspect of the invention provides a deuterium-enriched compound of Formula I:

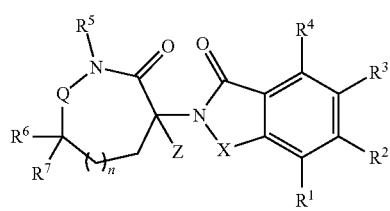

(I)

or a pharmaceutically acceptable salt, solvate, or stereoisomer thereof, wherein:

Z is H or D, provided that the abundance of deuterium in Z is at least 30%;

X is —C(R$^5$)$_2$—, —C(R$^5$)H—, —CH$_2$—, —C(O)—, —C(S)—, or ψ—C(C(R$^8$)$_3$)=N—, where ψ is a bond to the amide nitrogen atom;

Q is —C(R$^5$)$_2$—, —C(R$^5$)H—, —CH$_2$—, —C(O)—, —C(S)—, —S(O)—, or —S(O)$_2$—;

n is 1 or 2;

R$^1$, R$^2$, R$^3$, and R$^4$, are each independently selected from the group consisting of H, D, hydroxyl, halogen, cyano, nitro, optionally substituted amino, optionally substituted C-amido, optionally substituted N-amido, optionally substituted ester, optionally substituted sulfonyl, optionally substituted S-sulfonamido, optionally substituted N-sulfonamido, optionally substituted sulfonate, optionally substituted O-thiocarbamyl, optionally substituted N-thiocarbamyl, optionally substituted N-carbamyl, optionally substituted O-carbamyl, optionally substituted urea, optionally substituted thiourea, optionally substituted (C$_1$-C$_6$)-alkoxy, optionally substituted (C$_1$-C$_6$)-alkyl, optionally substituted (C$_2$-C$_6$)-alkenyl, optionally substituted (C$_2$-C$_6$)-alkynyl, optionally substituted (C$_3$-C$_8$)-carbocyclyl, optionally substituted (C$_6$-C$_{10}$)-aryl, optionally substituted (C$_3$-C$_8$)-heterocyclyl, and optionally substituted (C$_6$-C$_{10}$)-heteroaryl;

R$^5$ is selected from the group consisting of H, D, oxo, optionally substituted (C$_1$-C$_6$)-alkyl, optionally substituted (C$_2$-C$_6$)-alkenyl, optionally substituted (C$_2$-C$_6$)-alkynyl, optionally substituted (C$_3$-C$_8$)-carbocyclyl, optionally substituted (C$_6$-C$_{10}$)-aryl, optionally substituted (C$_3$-C$_8$)-heterocyclyl, and optionally substituted (C$_6$-C$_{10}$)-heteroaryl;

R$^6$, R$^7$, and R$^8$ are independently H or D; and any hydrogen atom may be optionally replaced with D.

Another aspect of the invention provides a deuterium-enriched compound of Formula II:

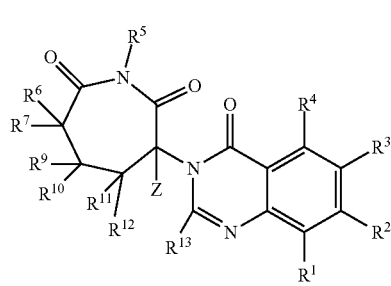

(II)

or a pharmaceutically acceptable salt, solvate, or stereoisomer thereof, wherein:

Z is H or D, provided that the abundance of deuterium in Z is at least 30%;

R$^5$, R$^6$, R$^7$, R$^9$, R$^{10}$, R$^{11}$, and R$^{12}$ are each independently selected from H and D;

R$^{13}$ is selected from: H; D; halo, —(CH$_2$)$_n$OH, phenyl, —O(C$_1$-C$_6$)alkyl, and (C$_1$-C$_6$)alkyl optionally substituted with one or more halo;

R$^1$, R$^2$, R$^3$, R$^4$ are each independently selected from: H, D, halo, hydroxyl, —NR$^b$R$^c$, —(CH$_2$)$_n$OH, (C$_1$-C$_6$) alkyl optionally substituted with one or more halo, ($C_1$-$C_6$)alkoxy optionally substituted with one or more halo, —$(CH_2)_n$NHR$^a$, R$^{14a}$, R$^{14b}$, and R$^{14c}$;

alternatively, two of R$^1$, R$^2$, R$^3$, and R$^4$ are taken together with the atoms to which they are attached to form a 5-6 membered carbocyclic or heterocyclic ring optionally substituted with one or more groups independently selected from halo, ($C_1$-$C_6$)alkyl optionally substituted with one or more halo, and ($C_1$-$C_6$)alkoxy optionally substituted with one or more halo R$^a$ is selected from: H, D, ($C_1$-$C_6$)alkyl optionally substituted with one or more halo, —$(CH_2)_n$-(6 to 10 membered aryl), —C(O)$(CH_2)_n$-(6 to 10 membered aryl), —C(O)$(CH_2)_n$-(6 to 10 membered heteroaryl), —C(O)($C_1$-$C_8$)alkyl optionally substituted with one or more halo, —C(O)$(CH_2)_n$—($C_3$-$C_{10}$-cycloalkyl), —C(O)$(CH_2)_n$—NR$^b$R$^c$, —C(O)$(CH_2)_n$—O—($C_1$-$C_6$)alkyl, and —C(O)$(CH_2)_n$—O—$(CH_2)_n$-(6 to 10 membered aryl); wherein the aryl and heteroaryl are optionally substituted with one or more groups selected from: halo, —SCF$_3$, ($C_1$-$C_6$)alkyl optionally substituted with one or more halo, and ($C_1$-$C_6$)alkoxy optionally substituted with one or more halo;

R$^b$ and R$^c$ are each independently selected from: H, D, ($C_1$-$C_6$)alkyl optionally substituted with one or more halo, ($C_1$-$C_6$)alkoxy optionally substituted with one or more halo, and 6 to 10 membered aryl; wherein the aryl is optionally substituted with one or more groups selected from: halo, ($C_1$-$C_6$)alkyl optionally substituted with one or more halo, and ($C_1$-$C_6$)alkoxy optionally substituted with one or more halo;

R$^{14a}$ is selected from: H, D, halo, —$(CH_2)_n$OH, ($C_1$-$C_6$) alkyl optionally substituted with one or more halo, and ($C_1$-$C_6$)alkoxy optionally substituted with one or more halo;

R$^{14b}$=—$(CH_2)_n$—NHR$^d$;

R$^{14c}$=—$(CH_2)_n$—NHR$^x$;

R$^d$ is selected from: H, D, —($C_1$-$C_6$)alkyl optionally substituted with one or more halo, —C(O)($C_1$-$C_8$)alkyl optionally substituted with one or more halo, —C(O)$(CH_2)_n$($C_3$-$C_{10}$-cycloalkyl), —C(O)$(CH_2)_n$NR$^e$R$^f$, and —C(O)$(CH_2)_n$O($C_1$-$C_6$)alkyl;

R$^e$ and R$^f$ are each independently selected from: hydrogen; ($C_1$-$C_6$)alkyl optionally substituted with one or more halo; and ($C_1$-$C_6$)alkoxy optionally substituted with one or more halo;

R$^x$ is selected from: —C(O)$(CH_2)_n$NHR$^h$; —$(CH_2)_n$-(6 to 10 membered aryl); —C(O)$(CH_2)_n$-(6 to 10 membered aryl); —C(O)$(CH_2)_n$-(6 to 10 membered heteroaryl); and, —C(O)$(CH_2)_n$O$(CH_2)_n$-(6 to 10 membered aryl), wherein the aryl and heteroaryl are optionally substituted with one or more groups selected from: halo; —SCF$_3$; ($C_1$-$C_6$)alkyl optionally substituted with one or more halo; and, ($C_1$-$C_6$)alkoxy substituted with one or more halo;

R$^h$ is selected from: 6 to 10 membered aryl optionally substituted with one or more groups selected from: halo; ($C_1$-$C_6$)alkyl optionally substituted with one or more halo;

and, ($C_1$-$C_6$)alkoxy optionally substituted with one or more halo;

n is independently selected from selected from 0, 1, and 2; and a hydrogen atom present in any substituent is optionally replaced by D.

Another aspect of the invention provides a deuterium-enriched compound of Formula II-X:

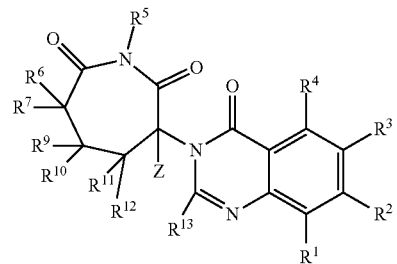

(II-X)

or a pharmaceutically acceptable salt, solvate, or stereoisomer thereof, wherein:

Z is H or D, provided that the abundance of deuterium in Z is at least 30%;

R$^5$, R$^6$, R$^7$, R$^9$, R$^{10}$, R$^{11}$, and R$^{12}$ are each independently selected from H and D;

R$^{13}$ is selected from: H; D; halo, —$(CH_2)_n$OH, phenyl, —O($C_1$-$C_6$)alkyl, and ($C_1$-$C_6$)alkyl optionally substituted with one or more halo;

R$^1$, R$^2$, R$^3$, R$^4$ are each independently selected from: H, D, halo, hydroxyl, —NR$^b$R$^c$, —$(CH_2)_n$OH, ($C_1$-$C_6$) alkyl optionally substituted with one or more halo, ($C_1$-$C_6$)alkoxy optionally substituted with one or more halo, —$(CH_2)_n$NHR$^a$, R$^{14a}$, R$^{14b}$, and R$^{14c}$;

alternatively, two of R$^1$, R$^2$, R$^3$, and R$^4$ are taken together with the atoms to which they are attached to form a 5-6 membered carbocyclic or heterocyclic ring optionally substituted with one or more groups independently selected from halo, ($C_1$-$C_6$)alkyl optionally substituted with one or more halo, and ($C_1$-$C_6$)alkoxy optionally substituted with one or more halo R$^a$ is selected from: H, D, ($C_1$-$C_6$)alkyl optionally substituted with one or more halo, —$(CH_2)_n$-(6 to 10 membered aryl), —C(O) $(CH_2)_n$-(6 to 10 membered aryl), —C(O)$(CH_2)_n$-(6 to 10 membered heteroaryl), —C(O)($C_1$-$C_8$)alkyl optionally substituted with one or more halo, —C(O)$(CH_2)_n$—($C_3$-$C_{10}$-cycloalkyl), —C(O)$(CH_2)_n$—NR$^b$R$^c$, —C(O)$(CH_2)_n$—O—($C_1$-$C_6$)alkyl, and —C(O)$(CH_2)_n$—O—$(CH_2)_n$-(6 to 10 membered aryl); wherein the aryl and heteroaryl are optionally substituted with one or more groups selected from: halo, —SCF$_3$, ($C_1$-$C_6$)alkyl optionally substituted with one or more halo, and ($C_1$-$C_6$)alkoxy optionally substituted with one or more halo;

R$^b$ and R$^c$ are each independently selected from: H, D, ($C_1$-$C_6$)alkyl optionally substituted with one or more halo, ($C_1$-$C_6$)alkoxy optionally substituted with one or more halo, and 6 to 10 membered aryl; wherein the aryl is optionally substituted with one or more groups selected from: halo, ($C_1$-$C_6$)alkyl optionally substituted with one or more halo, and ($C_1$-$C_6$)alkoxy optionally substituted with one or more halo;

R$^{14a}$ is selected from: H, D, halo, —$(CH_2)_n$OH, ($C_1$-$C_6$) alkyl optionally substituted with one or more halo, and ($C_1$-$C_6$)alkoxy optionally substituted with one or more halo;

R$^{14b}$=—$(CH_2)_n$—NHR$^d$;

R$^{14c}$=—$(CH_2)_n$—NHR$^x$;

R$^d$ is selected from: H, D, —($C_1$-$C_6$)alkyl optionally substituted with one or more halo, —C(O)($C_1$-$C_8$)alkyl optionally substituted with one or more halo, —C(O) $(CH_2)_n$($C_3$-$C_{10}$-cycloalkyl), —C(O)$(CH_2)_n$NR$^e$R$^f$, and —C(O)$(CH_2)_n$O($C_1$-$C_6$)alkyl;

$R^e$ and $R^f$ are each independently selected from: hydrogen; $(C_1-C_6)$alkyl optionally substituted with one or more halo; and $(C_1-C_6)$alkoxy optionally substituted with one or more halo;

$R^x$ is selected from: —C(O)(CH$_2$)$_n$NHR$^h$; —(CH$_2$)$_n$-(6 to 10 membered aryl); —C(O)(CH$_2$)$_n$-(6 to 10 membered aryl); —C(O)(CH$_2$)$_n$-(6 to 10 membered heteroaryl); and, —C(O)(CH$_2$)$_n$O(CH$_2$)$_n$-(6 to 10 membered aryl), wherein the aryl and heteroaryl are optionally substituted with one or more groups selected from: halo; —SCF$_3$; $(C_1-C_6)$alkyl optionally substituted with one or more halo; and, $(C_1-C_6)$alkoxy substituted with one or more halo;

$R^h$ is selected from: 6 to 10 membered aryl optionally substituted with one or more groups selected from: halo; $(C_1-C_6)$alkyl optionally substituted with one or more halo;

and, $(C_1-C_6)$alkoxy optionally substituted with one or more halo; and n is independently selected from selected from 0, 1, and 2.

In certain embodiments, the compound is a compound of Formula I, II, or II-X.

Formulas I, II, and II-X may be further described according to one or more of the definitions for the variables provided below. In particular, collections of compounds defined by combinations of particular definitions (provided below) for each of the variables are contemplated.

In certain embodiments, X is —CH$_2$—, —C(O)—, or ψ—C(CH$_3$)=N—, where ψ is a bond to the amide nitrogen atom. In certain other embodiments, X is ψ-C(CD$_3$)=N—, where ψ is a bond to the amide nitrogen atom. In certain embodiments, X is —CH$_2$—. In certain other embodiments, X is —C(O)—. In certain other embodiments, X is ψ-C(C(R$^8$)$_3$)=N—, where ψ is a bond to the amide nitrogen atom.

In certain embodiments, Q is —C(O)—. In certain other embodiments, Q is —CH$_2$—.

In certain embodiments, n is 1.

In certain embodiments, R$^1$ is selected from the group consisting of H, D, and optionally substituted amino. In certain embodiments, R$^1$ is H. In certain other embodiments, R$^1$ is D. In certain other embodiments, R$^1$ is optionally substituted amino. In certain embodiments, R$^1$ is NH$_2$.

In certain embodiments, R$^2$ is selected from the group consisting of H, D, and optionally substituted $(C_1-C_6)$-alkyl. In certain embodiments, R$^2$ is H. In certain other embodiments, R$^2$ is D. In certain other embodiments R$^2$ is optionally substituted $(C_1-C_6)$-alkyl.

In certain more specific embodiments, R$^2$ is

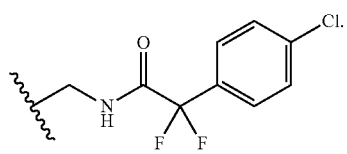 [SMILES: *CNC(=O)C(F)(F)c1ccc(Cl)cc1]

In certain embodiments, R$^3$ is H or D. In certain embodiments, R is H.

In certain embodiments, R$^4$ is selected from the group consisting of H, D, and optionally substituted amino. In certain embodiments, R$^4$ is H. In certain other embodiments, R$^4$ is D. In certain other embodiments, R$^4$ is optionally substituted amino. In certain embodiments, R$^4$ is NH$_2$.

In certain embodiments, each occurrence of R$^5$ is independently selected from the group consisting of H and D. In certain embodiments, R$^5$ is H. In certain other embodiments, R$^5$ is D.

In certain embodiments, R$^6$ and R$^7$ are D. In certain other embodiments, R$^6$ and R$^7$ are H.

In certain embodiments, R$^8$ is D. In certain other embodiments, R$^8$ is H.

In certain embodiments, the foregoing compounds are provided in stereochemically pure form, such as having an enantiomeric excess or a diastereomeric excess greater than 90%, 95%, 98% or 99%. In certain embodiments, the predominant stereoisomer has the R-configuration at the carbon atom bearing Z. In certain other embodiments, the predominant stereoisomer has the S-configuration at the carbon atom bearing Z.

In certain embodiments, the deuterium-enriched compound is a compound of Formula II-Y represented by:

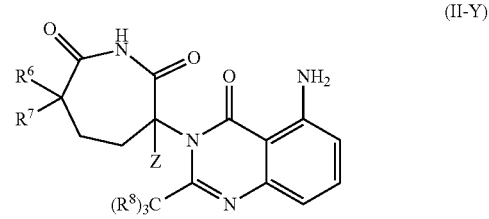

(II-Y)

or a pharmaceutically acceptable salt, solvate, or stereoisomer thereof; wherein Z is H or D, provided that the abundance of deuterium in Z is at least 30%;

R$^6$, R$^7$, and R$^8$ are independently H or D;

and any hydrogen atom may be optionally replaced with D.

In certain embodiments, R$^6$ and R$^7$ are D. In certain other embodiments, R$^6$ and R$^7$ are H.

In certain embodiments, R$^8$ is D. In certain other embodiments, R$^8$ is H.

In certain embodiments, the deuterium-enriched compound is a compound of Formula II-A represented by:

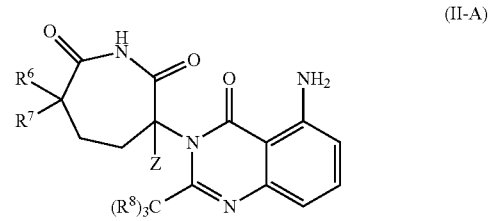

(II-A)

or a pharmaceutically acceptable salt, solvate, or stereoisomer thereof; wherein Z is H or D, provided that the abundance of deuterium in Z is at least 30%; and R$^6$, R$^7$, and R$^8$ are independently H or D.

In certain embodiments, R$^6$ and R$^7$ are D. In certain other embodiments, R$^6$ and R$^7$ are H.

In certain embodiments, R$^8$ is D. In certain other embodiments, R$^8$ is H.

In certain embodiments, the deuterium-enriched compound is a compound of Formula II-B represented by:

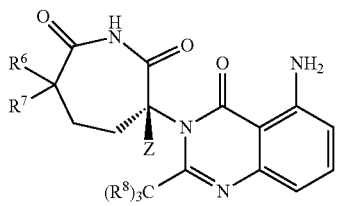

(II-B)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$, $R^7$, and $R^8$ are independently H or D.

In certain embodiments, $R^6$ and $R^7$ are D. In certain other embodiments, $R^6$ and $R^7$ are H.

In certain embodiments, $R^8$ is D. In certain other embodiments, $R^8$ is H.

In certain embodiments, the deuterium-enriched compound is a compound of Formula II-C represented by:

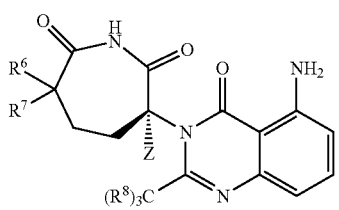

(II-C)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$, $R^7$, and $R^8$ are independently H or D.

In certain embodiments, $R^6$ and $R^7$ are D. In certain other embodiments, $R^6$ and $R^7$ are H.

In certain embodiments, $R^8$ is D. In certain other embodiments, $R^8$ is H.

In certain embodiments, the deuterium-enriched compound is a compound of Formula II-D represented by:

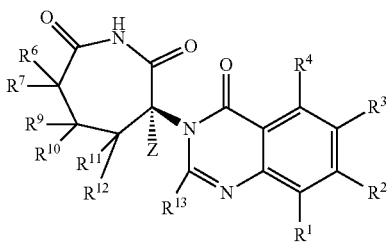

(II-D)

or a pharmaceutically acceptable salt, solvate, or stereoisomer thereof; wherein the compound has a stereochemical purity of at least 75% enantiomeric excess at the carbon atom bearing variable Z.

In certain embodiments, $R^6$ and $R^7$ are D. In certain other embodiments, $R^6$ and $R^7$ are H.

In certain embodiments, the deuterium-enriched compound is a compound of Formula II-E represented by:

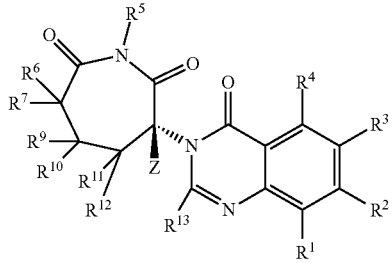

(II-E)

or a pharmaceutically acceptable salt, solvate, or stereoisomer thereof; wherein the compound has a stereochemical purity of at least 75% enantiomeric excess at the carbon atom bearing variable Z.

In certain embodiments, $R^6$ and $R^7$ are D. In certain other embodiments, $R^6$ and $R^7$ are H.

In certain embodiments, the deuterium-enriched compound is a compound of Formula II-F represented by:

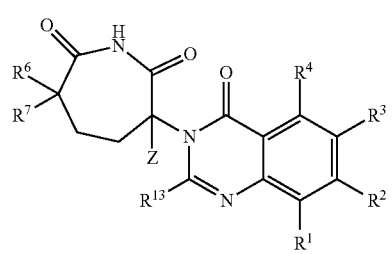

(II-F)

or a pharmaceutically acceptable salt, solvate, or stereoisomer thereof; wherein Z is H or D, provided that the abundance of deuterium in Z is at least 30%; $R^6$ and $R^7$ are independently H or D; $R^{13}$ is $CH_3$ or $CD_3$; and any hydrogen atom may be optionally replaced with D.

In certain embodiments, $R^6$ and $R^7$ are D. In certain other embodiments, $R^6$ and $R^7$ are H.

In certain embodiments, the deuterium-enriched compound is a compound of Formula II-G represented by:

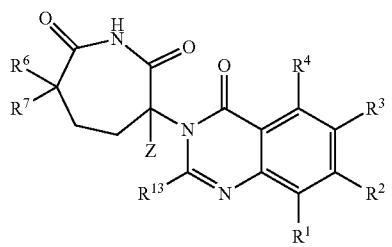

(II-G)

or a pharmaceutically acceptable salt, solvate, or stereoisomer thereof; wherein Z is H or D, provided that the abundance of deuterium in Z is at least 30%; $R^6$ and $R^7$ are independently H or D; $R^{13}$ is $CH_3$ or $CD_3$.

In certain embodiments, $R^6$ and $R^7$ are D. In certain other embodiments, $R^6$ and $R^7$ are H.

In certain embodiments, the deuterium-enriched compound is a compound of Formula II-H represented by:

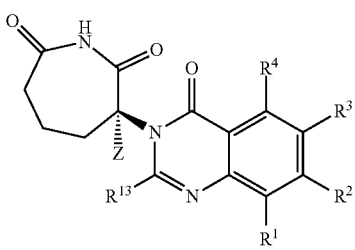

(II-H)

or a pharmaceutically acceptable salt or solvate thereof; wherein the compound has a stereochemical purity of at least 75% enantiomeric excess at the carbon atom bearing variable Z; and $R^{13}$ is $CH_3$ or $CD_3$.

In certain embodiments, the deuterium-enriched compound is a compound of Formula II-J represented by:

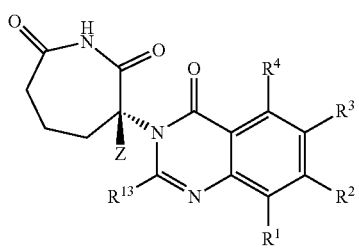

(II-J)

or a pharmaceutically acceptable salt or solvate thereof; wherein the compound has a stereochemical purity of at least 75% enantiomeric excess at the carbon atom bearing variable Z; and $R^{13}$ is $CH_3$ or $CD_3$.

In some embodiments of formulas I and II, and subformulas thereof, $R^8$ is D. In other embodiments, $R^8$ is H. In some embodiments, $R^6$ and $R^7$ are D. In some embodiments, $R^6$ and $R^7$ are H.

In some embodiments of formulas I and II, and subformulas thereof, $R^1$, $R^2$, and $R^4$ are each independently selected from H and D. In some embodiments, $R^1$, $R^2$, and $R^4$ are each H. In some embodiments $R^3$ is $(C_1-C_6)$alkyl, e.g., methyl. In some embodiments, $R^3$ is —$CH_2$—$NHR^a$. In some embodiments, $R^1$, $R^2$, and $R^4$ are each independently selected from H and D; and $R^3$ is $(C_1-C_6)$alkyl, e.g., methyl, or $R^3$ is —$CH_2$—$NHR^a$. In some embodiments, $R^1$, $R^2$, and $R^4$ are each H; and $R^3$ is $(C_1-C_6)$alkyl, e.g., methyl, or $R^3$ is —$CH_2$—$NHR^a$.

In some embodiments of formulas I and II, and subformulas thereof, $R^1$, $R^3$, and $R^4$ are each independently selected from H and D. In some embodiments, $R^1$, $R^3$, and $R^4$ are each H. In some embodiments $R^2$ is halo, e.g., chloro. In some embodiments, $R^1$, $R^3$, and $R^4$ are each independently selected from H and D; and $R^2$ is halo, e.g., chloro. In some embodiments, $R^1$, $R^3$, and $R^4$ are each H; and $R^2$ is halo, e.g., chloro.

In some embodiments of formulas I and II, and subformulas thereof, $R^2$, $R^3$, and $R^4$ are each independently selected from H and D. In some embodiments, $R^2$, $R^3$, and $R^4$ are each H. In some embodiments $R^1$ is hydroxyl. In some embodiments, $R^2$, $R^3$, and $R^4$ are each independently selected from H and D; and $R^1$ is hydroxyl. In some embodiments, $R^2$, $R^3$, and $R^4$ are each H; and $R^1$ is hydroxyl.

In certain embodiments, the deuterium-enriched compound is a compound of Formula III represented by:

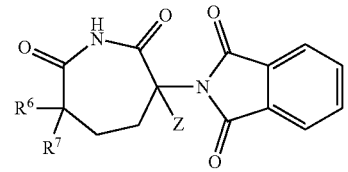

(III)

or a pharmaceutically acceptable salt, solvate, or stereoisomer thereof; wherein Z is H or D, provided that the abundance of deuterium in Z is at least 30%; $R^6$ and $R^7$ are independently H or D; and any hydrogen atom may be optionally replaced with D.

In certain embodiments, $R^6$ and $R^7$ are D. In certain other embodiments, $R^6$ and $R^7$ are H.

In certain embodiments, the deuterium-enriched compound is a compound of Formula III-A represented by:

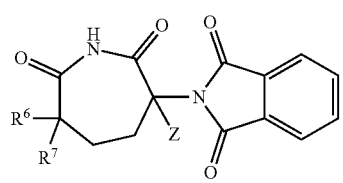

(III-A)

or a pharmaceutically acceptable salt, solvate, or stereoisomer thereof; wherein Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula III-B represented by:

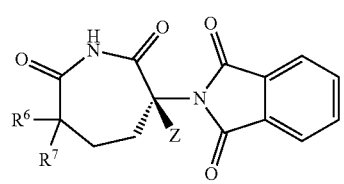

(III-B)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula III-C represented by:

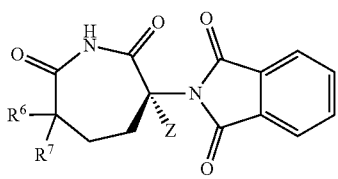

(III-C)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula IV represented by:

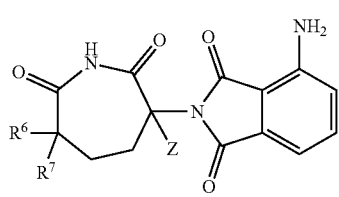

(IV)

or a pharmaceutically acceptable salt, solvate, or stereoisomer thereof; wherein Z is H or D, provided that the abundance of deuterium in Z is at least 30%; $R^6$ and $R^7$ are independently H or D; and any hydrogen atom may be optionally replaced with D.

In certain embodiments, $R^6$ and $R^7$ are D. In certain other embodiments, $R^6$ and $R^7$ are H.

In certain embodiments, the deuterium-enriched compound is a compound of Formula IV-A represented by:

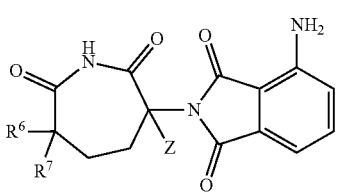

(IV-A)

or a pharmaceutically acceptable salt, solvate, or stereoisomer thereof; wherein Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula IV-B represented by:

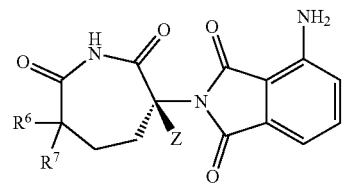

(IV-B)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula IV-C represented by:

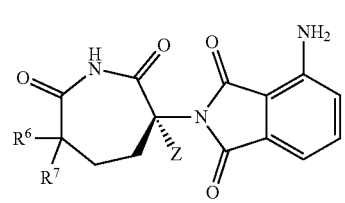

(IV-C)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula V represented by:

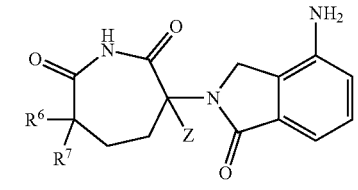

(V)

or a pharmaceutically acceptable salt, solvate, or stereoisomer thereof; wherein Z is H or D, provided that the abundance of deuterium in Z is at least 30%; $R^6$ and $R^7$ are independently H or D; and any hydrogen atom may be optionally replaced with D.

In certain embodiments, $R^6$ and $R^7$ are D. In certain other embodiments, $R^6$ and $R^7$ are H.

In certain embodiments, the deuterium-enriched compound is a compound of Formula V-A represented by:

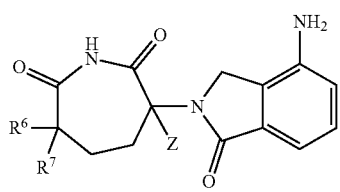

(V-A)

or a pharmaceutically acceptable salt, solvate, or stereoisomer thereof; wherein Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula V-B represented by:

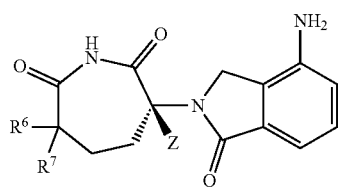

(V-B)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula V-C represented by:

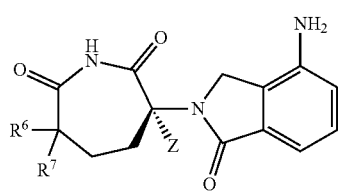

(V-C)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula VI represented by:

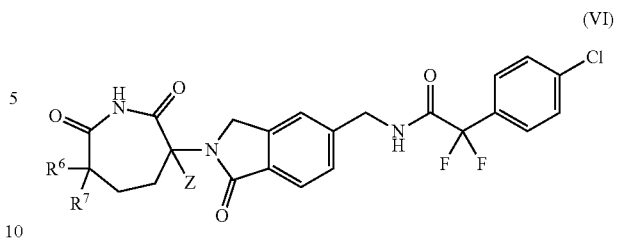

(VI)

or a pharmaceutically acceptable salt, solvate, or stereoisomer thereof; wherein Z is H or D, provided that the abundance of deuterium in Z is at least 30%; $R^6$ and $R^7$ are independently H or D; and any hydrogen atom may be optionally replaced with D.

In certain embodiments, $R^6$ and $R^7$ are D. In certain other embodiments, $R^6$ and $R^7$ are H.

In certain embodiments, the deuterium-enriched compound is a compound of Formula VI-A represented by:

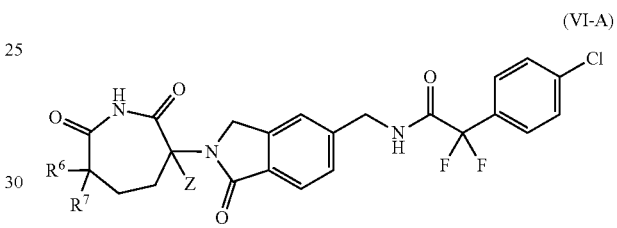

(VI-A)

or a pharmaceutically acceptable salt, solvate, or stereoisomer thereof; wherein Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula VI-B represented by:

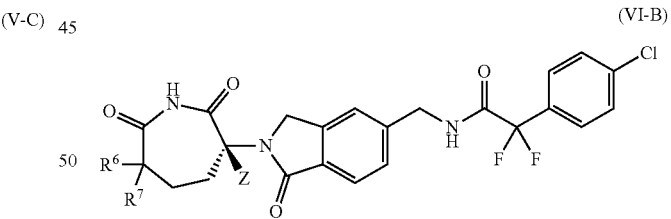

(VI-B)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

In certain embodiments, the deuterium-enriched compound is a compound of Formula VI-C represented by:

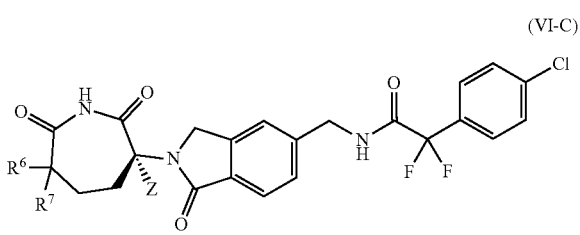

(VI-C)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and $R^6$ and $R^7$ are independently H or D.

In certain embodiments, $R^6$ and $R^7$ are D. In certain other embodiments, $R^6$ and $R^7$ are H.

Deuterium-enriched compounds of the above Formulae (e.g., Formula I, II, II-A, II-B, II-C, III, III-A, III-B, III-C, IV, IV-A, IV-B, IV-C, V, V-A, V-B, V-C, VI, VI-A, VI-B, and VI-C) may be further characterized according to the extent of deuterium enrichment at the position defined by variable Z and/or the stereochemical purity of the compound at the position defined by variable Z. For example, in certain embodiments, the abundance of deuterium in Z is at least 60%. In certain other embodiments, the abundance of deuterium in Z is at least 75%. In yet other embodiments, the abundance of deuterium in Z is at least 90%. In yet other embodiments, the abundance of deuterium in Z is at least 95%. In yet other embodiments, the abundance of deuterium in Z is at least 98%. In yet other embodiments, the abundance of deuterium in Z is from about 80% to about 99%, about 85% to about 99%, or about 90% to about 99%. In yet other embodiments, the abundance of deuterium in Z is selected from: (a) at least 40%, (b) at least 50%, (c) at least 60%, (d) at least 70%, (e) at least 75%, (f) at least 80%, (g) at least 90%, (h) at least 95%, (i) at least 97%, and (j) about 100%. Additional examples of the abundance of deuterium in Z include about 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%.

In certain embodiments, the compound has a stereochemical purity of at least 85% enantiomeric excess at the carbon atom bearing variable Z. In certain other embodiments, the compound has a stereochemical purity of at least 90% enantiomeric excess at the carbon atom bearing variable Z. In certain other embodiments, the compound has a stereochemical purity of at least 95% enantiomeric excess at the carbon atom bearing variable Z. In certain other embodiments, the compound has a stereochemical purity of at least 98% enantiomeric excess at the carbon atom bearing variable Z. In certain other embodiments, the compound has a stereochemical purity of at least 99% enantiomeric excess at the carbon atom bearing variable Z. In other embodiments, the deuterium-enriched compound has a stereochemical purity of at least 80%, 85%, 90%, 95%, or 98% enantiomeric excess at a chiral carbon atom bearing variable Z, and yet additional examples of stereochemical purity include an enantiomeric excess of at least 71, 72, 73, 74, 75, 76, 77, 78, 79, 80, 81, 82, 83, 84, 85, 86, 87, 88, 89, 90, 91, 92, 93, 94, 95, 96, 97, 98, or 99% at a chiral carbon atom bearing variable Z.

In yet other embodiments, a deuterium-enriched compound may contain one or more stereogenic centers in addition to the stereogenic center at the carbon atom bearing variable Z, and such deuterium-enriched compounds may be provided in stereochemically pure form, such as where the compound has an overall stereochemical purity of at least 90%, 95%, 98% or 99%, which may be expressed as a diastereomeric excess of at least 90%, 95%, 98% or 99%.

In certain embodiments, the deuterium-enriched compound is a compound in Table 1 or a pharmaceutically acceptable salt thereof.

TABLE 1

| No. | Chemical Structure |
|---|---|
| 101 | 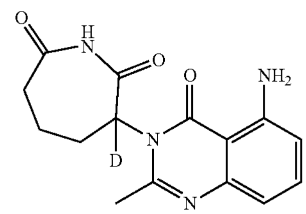 [SMILES: [2H]C1(n2c(C)nc3cccc(N)c3c2=O)CCCC(=O)NC1=O] |
| 102 | 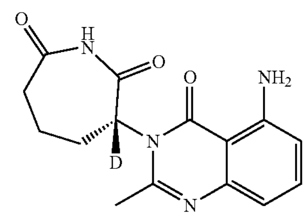 [SMILES: [2H][C@@]1(n2c(C)nc3cccc(N)c3c2=O)CCCC(=O)NC1=O] |
| 103 | 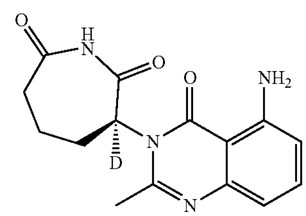 [SMILES: [2H][C@]1(n2c(C)nc3cccc(N)c3c2=O)CCCC(=O)NC1=O] |
| 104 | 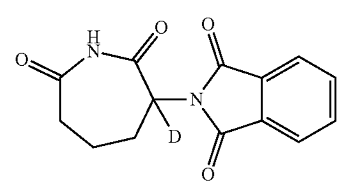 [SMILES: [2H]C1(N2C(=O)c3ccccc3C2=O)CCCC(=O)NC1=O] |
| 105 | 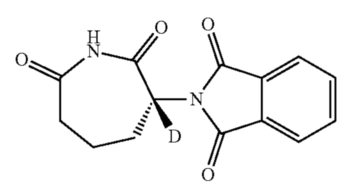 [SMILES: [2H][C@@]1(N2C(=O)c3ccccc3C2=O)CCCC(=O)NC1=O] |
| 106 | 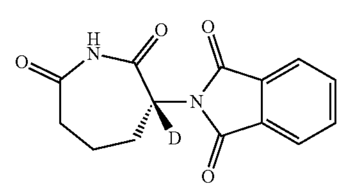 [SMILES: [2H][C@@]1(N2C(=O)c3ccccc3C2=O)CCCC(=O)NC1=O] |

TABLE 1-continued

| No. | Chemical Structure |
|---|---|
| 107 | 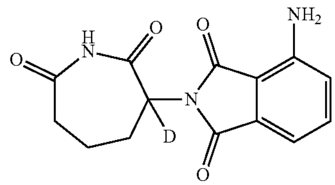 [SMILES: [2H]C1(N2C(=O)c3cccc(N)c3C2=O)CCCC(=O)NC1=O] |
| 108 | 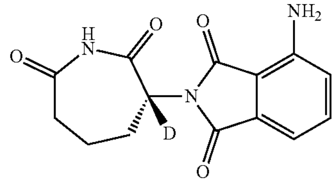 [SMILES: [2H][C@@]1(N2C(=O)c3cccc(N)c3C2=O)CCCC(=O)NC1=O] |
| 109 | 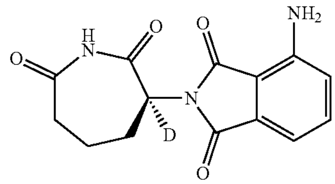 [SMILES: [2H][C@]1(N2C(=O)c3cccc(N)c3C2=O)CCCC(=O)NC1=O] |
| 110 | 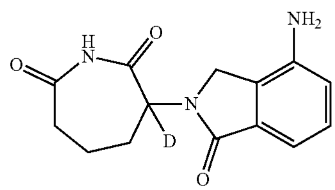 [SMILES: [2H]C1(N2Cc3c(N)cccc3C2=O)CCCC(=O)NC1=O] |
| 111 | 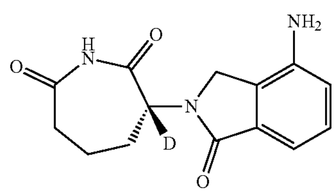 [SMILES: [2H][C@@]1(N2Cc3c(N)cccc3C2=O)CCCC(=O)NC1=O] |
| 112 | 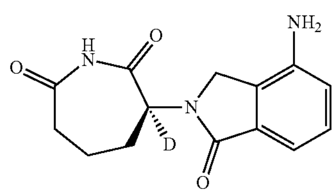 [SMILES: [2H][C@]1(N2Cc3c(N)cccc3C2=O)CCCC(=O)NC1=O] |
| 113 | 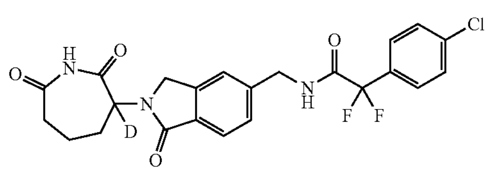 [SMILES: [2H]C1(N2Cc3cc(CNC(=O)C(F)(F)c4ccc(Cl)cc4)ccc3C2=O)CCCC(=O)NC1=O] |
| 114 | 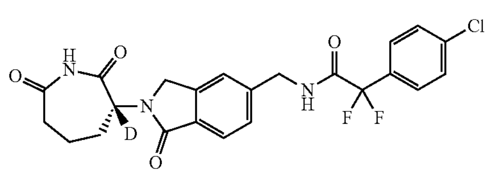 [SMILES: [2H][C@@]1(N2Cc3cc(CNC(=O)C(F)(F)c4ccc(Cl)cc4)ccc3C2=O)CCCC(=O)NC1=O] |
| 115 | 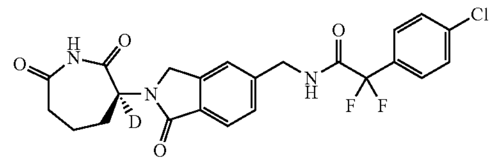 [SMILES: [2H][C@]1(N2Cc3cc(CNC(=O)C(F)(F)c4ccc(Cl)cc4)ccc3C2=O)CCCC(=O)NC1=O] |

In certain embodiments, the deuterium-enriched compound is a compound in Table 2 or a pharmaceutically acceptable salt thereof.

TABLE 2

| No. | Chemical Structure |
|---|---|
| 116 | 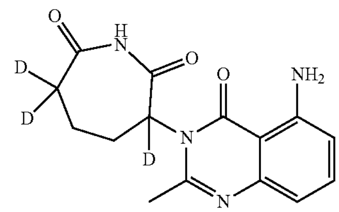 [SMILES: [2H]C1([2H])CCC([2H])(n2c(C)nc3cccc(N)c3c2=O)C(=O)NC1=O] |
| 117 | 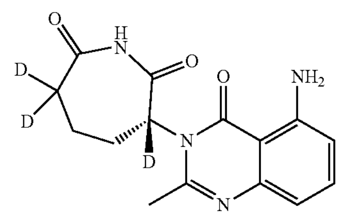 [SMILES: [2H]C1([2H])CC[C@@]([2H])(n2c(C)nc3cccc(N)c3c2=O)C(=O)NC1=O] |
| 118 | 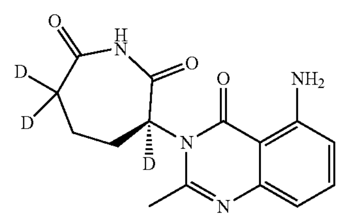 [SMILES: [2H]C1([2H])CC[C@]([2H])(n2c(C)nc3cccc(N)c3c2=O)C(=O)NC1=O] |
| 119 | 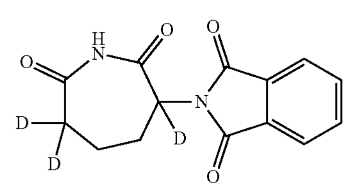 [SMILES: [2H]C1([2H])CCC([2H])(N2C(=O)c3ccccc3C2=O)C(=O)NC1=O] |
| 120 | 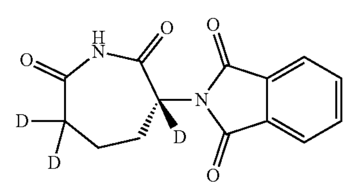 [SMILES: [2H]C1([2H])CC[C@@]([2H])(N2C(=O)c3ccccc3C2=O)C(=O)NC1=O] |
| 121 | 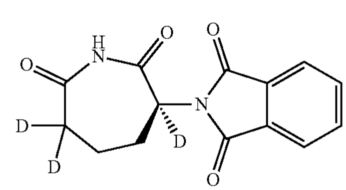 [SMILES: [2H]C1([2H])CC[C@]([2H])(N2C(=O)c3ccccc3C2=O)C(=O)NC1=O] |

TABLE 2-continued

| No. | Chemical Structure |
|-----|---------------------|
| 122 | 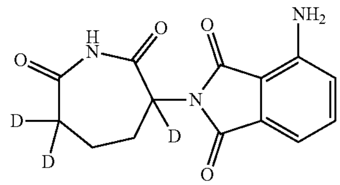 [SMILES: [2H]C1([2H])CCC([2H])(N2C(=O)c3cccc(N)c3C2=O)C(=O)NC1=O] |
| 123 | 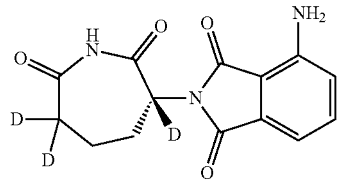 [SMILES: [2H]C1([2H])CC[C@@]([2H])(N2C(=O)c3cccc(N)c3C2=O)C(=O)NC1=O] |
| 124 | 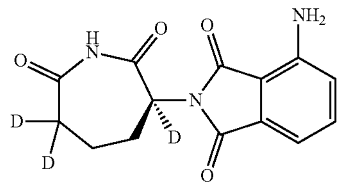 [SMILES: [2H]C1([2H])CC[C@]([2H])(N2C(=O)c3cccc(N)c3C2=O)C(=O)NC1=O] |
| 125 | 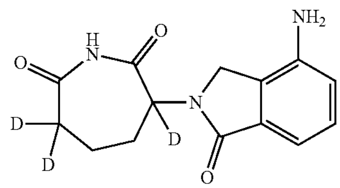 [SMILES: [2H]C1([2H])CCC([2H])(N2Cc3c(N)cccc3C2=O)C(=O)NC1=O] |
| 126 | 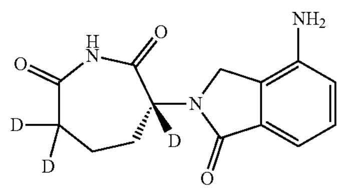 [SMILES: [2H]C1([2H])CC[C@@]([2H])(N2Cc3c(N)cccc3C2=O)C(=O)NC1=O] |
| 127 | 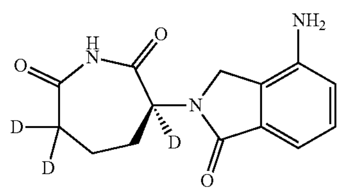 [SMILES: [2H]C1([2H])CC[C@]([2H])(N2Cc3c(N)cccc3C2=O)C(=O)NC1=O] |
| 128 | 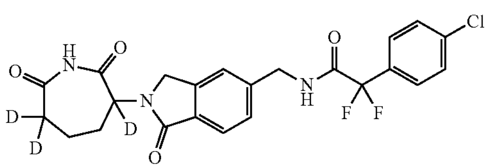 [SMILES: [2H]C1([2H])CCC([2H])(N2Cc3cc(CNC(=O)C(F)(F)c4ccc(Cl)cc4)ccc3C2=O)C(=O)NC1=O] |
| 129 | 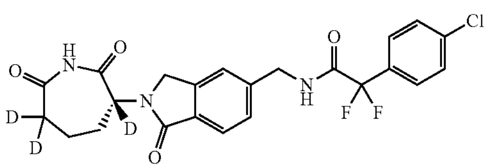 [SMILES: [2H]C1([2H])CC[C@@]([2H])(N2Cc3cc(CNC(=O)C(F)(F)c4ccc(Cl)cc4)ccc3C2=O)C(=O)NC1=O] |

TABLE 2-continued

| No. | Chemical Structure |
|-----|---------------------|
| 130 | |

In certain embodiments, the deuterium-enriched compound is a compound in Table 3 or a pharmaceutically acceptable salt thereof.

TABLE 3

| No. | Chemical Structure |
|-----|---------------------|
| 131 | 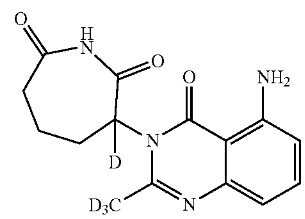 [SMILES: [2H]C([2H])([2H])c1nc2cccc(N)c2c(=O)n1C1([2H])CCCC(=O)NC1=O] |
| 132 | 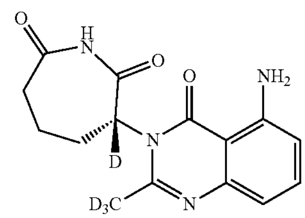 [SMILES: [2H]C([2H])([2H])c1nc2cccc(N)c2c(=O)n1[C@]1([2H])CCCC(=O)NC1=O] |
| 133 | 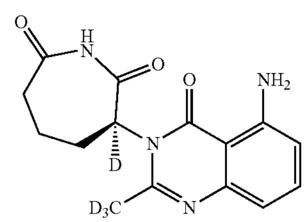 [SMILES: [2H]C([2H])([2H])c1nc2cccc(N)c2c(=O)n1[C@@]1([2H])CCCC(=O)NC1=O] |
| 134 | 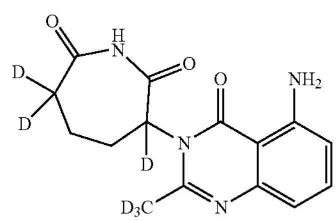 [SMILES: [2H]C1([2H])CCC([2H])(n2c(C([2H])([2H])[2H])nc3cccc(N)c3c2=O)C(=O)NC1=O] |
| 135 | 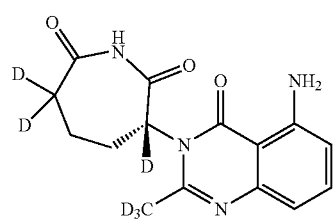 [SMILES: [2H]C1([2H])CC[C@@]([2H])(n2c(C([2H])([2H])[2H])nc3cccc(N)c3c2=O)C(=O)NC1=O] |

TABLE 3-continued
| No. | Chemical Structure |
|---|---|
| 136 | 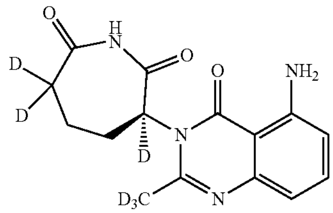 [SMILES: [2H]C1([2H])CC[C@]([2H])(n2c(C([2H])([2H])[2H])nc3cccc(N)c3c2=O)C(=O)NC1=O] |
In certain embodiments, the deuterium-enriched compound is a compound in Table 4 or a pharmaceutically acceptable salt thereof.
TABLE 4
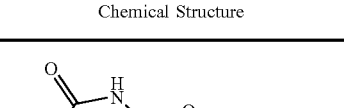
| No. | Chemical Structure |
|---|---|
| 137 | 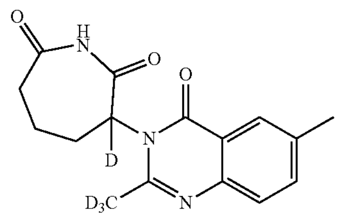 [SMILES: [2H]C([2H])([2H])c1nc2ccc(C)cc2c(=O)n1C1([2H])CCCC(=O)NC1=O] |
| 138 | 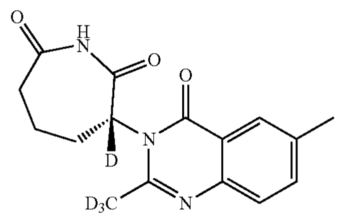 [SMILES: [2H]C([2H])([2H])c1nc2ccc(C)cc2c(=O)n1[C@]1([2H])CCCC(=O)NC1=O] |
| 139 | 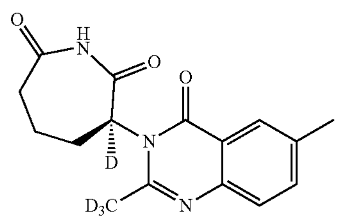 [SMILES: [2H]C([2H])([2H])c1nc2ccc(C)cc2c(=O)n1[C@@]1([2H])CCCC(=O)NC1=O] |
| 140 | 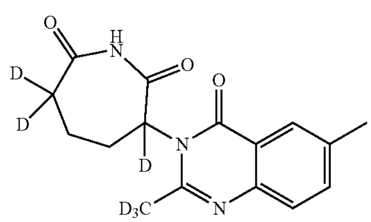 [SMILES: [2H]C1([2H])CCC([2H])(n2c(C([2H])([2H])[2H])nc3ccc(C)cc3c2=O)C(=O)NC1=O] |
| 141 | 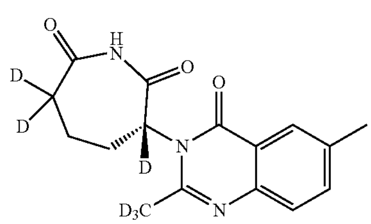 |
TABLE 4-continued
| No. | Chemical Structure |
|---|---|
| 142 | 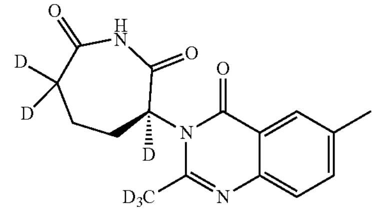 [SMILES: [2H]C1([2H])CC[C@]([2H])(n2c(C([2H])([2H])[2H])nc3ccc(C)cc3c2=O)C(=O)NC1=O] |
| 143 | 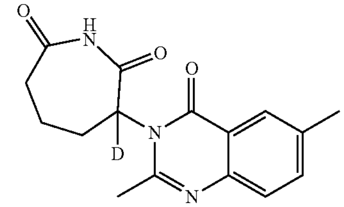 [SMILES: [2H]C1(n2c(C)nc3ccc(C)cc3c2=O)CCCC(=O)NC1=O] |
| 144 | 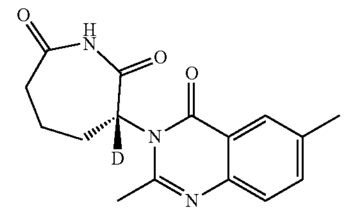 [SMILES: [2H][C@@]1(n2c(C)nc3ccc(C)cc3c2=O)CCCC(=O)NC1=O] |
| 145 | 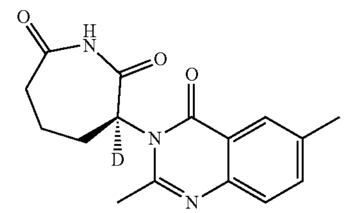 [SMILES: [2H][C@]1(n2c(C)nc3ccc(C)cc3c2=O)CCCC(=O)NC1=O] |
| 146 | 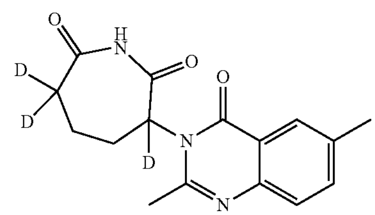 [SMILES: [2H]C1([2H])CCC([2H])(n2c(C)nc3ccc(C)cc3c2=O)C(=O)NC1=O] |
| 147 | 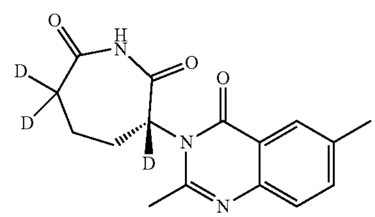 [SMILES: [2H]C1([2H])CC[C@@]([2H])(n2c(C)nc3ccc(C)cc3c2=O)C(=O)NC1=O] |
| 148 | 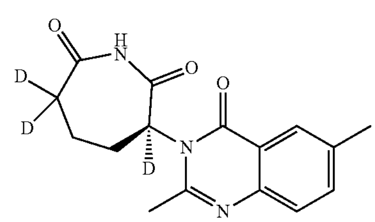 [SMILES: [2H]C1([2H])CC[C@]([2H])(n2c(C)nc3ccc(C)cc3c2=O)C(=O)NC1=O] |

In certain embodiments, the deuterium-enriched compound is a compound in Table 5 or a pharmaceutically acceptable salt thereof.

TABLE 5

| No. | Chemical Structure |
| --- | --- |
| 149 | 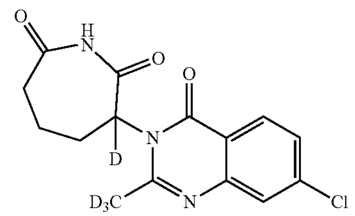 [SMILES: [2H]C([2H])([2H])c1nc2cc(Cl)ccc2c(=O)n1C1([2H])CCCC(=O)NC1=O] |
| 150 | 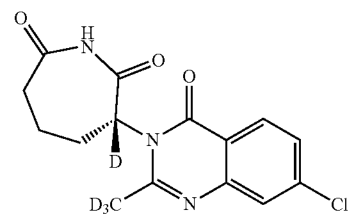 [SMILES: [2H]C([2H])([2H])c1nc2cc(Cl)ccc2c(=O)n1[C@]1([2H])CCCC(=O)NC1=O] |
| 151 | 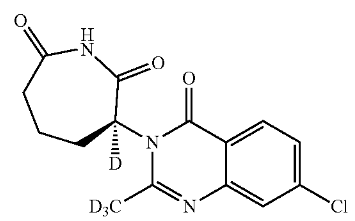 [SMILES: [2H]C([2H])([2H])c1nc2cc(Cl)ccc2c(=O)n1[C@@]1([2H])CCCC(=O)NC1=O] |
| 152 | 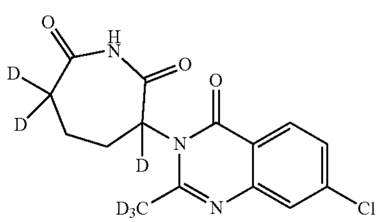 [SMILES: [2H]C1([2H])CCC([2H])(n2c(C([2H])([2H])[2H])nc3cc(Cl)ccc3c2=O)C(=O)NC1=O] |
| 153 | 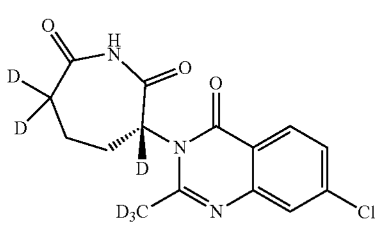 [SMILES: [2H]C1([2H])CC[C@@]([2H])(n2c(C([2H])([2H])[2H])nc3cc(Cl)ccc3c2=O)C(=O)NC1=O] |
| 154 | 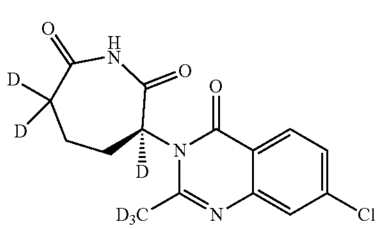 [SMILES: [2H]C1([2H])CC[C@]([2H])(n2c(C([2H])([2H])[2H])nc3cc(Cl)ccc3c2=O)C(=O)NC1=O] |

TABLE 5-continued

| No. | Chemical Structure |
| --- | --- |
| 155 | 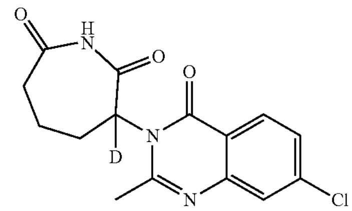 [SMILES: [2H]C1(n2c(C)nc3cc(Cl)ccc3c2=O)CCCC(=O)NC1=O] |
| 156 | 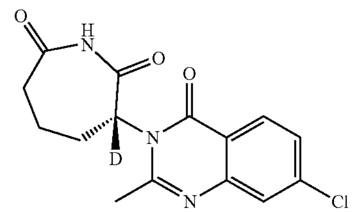 [SMILES: [2H][C@@]1(n2c(C)nc3cc(Cl)ccc3c2=O)CCCC(=O)NC1=O] |
| 157 | 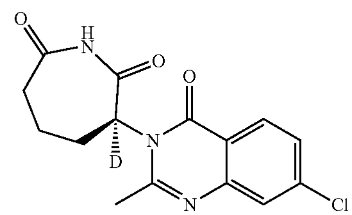 [SMILES: [2H][C@]1(n2c(C)nc3cc(Cl)ccc3c2=O)CCCC(=O)NC1=O] |
| 158 | 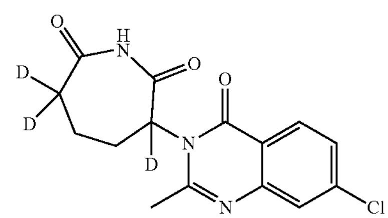 [SMILES: [2H]C1([2H])CCC([2H])(n2c(C)nc3cc(Cl)ccc3c2=O)C(=O)NC1=O] |
| 159 | 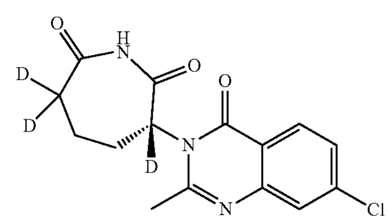 [SMILES: [2H]C1([2H])CC[C@@]([2H])(n2c(C)nc3cc(Cl)ccc3c2=O)C(=O)NC1=O] |
| 160 | 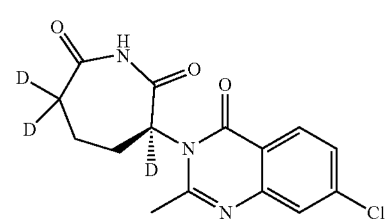 [SMILES: [2H]C1([2H])CC[C@]([2H])(n2c(C)nc3cc(Cl)ccc3c2=O)C(=O)NC1=O] |

In certain embodiments, the deuterium-enriched compound is a compound in Table 6 or a pharmaceutically acceptable salt thereof.

TABLE 6

| No. | Chemical Structure |
|-----|---|
| 161 | (structure) |
| 162 | (structure) |
| 163 | (structure) |
| 164 | (structure) |
| 165 | (structure) |
| 166 | (structure) |
| 167 | (structure) |
| 168 | (structure) |
| 169 | (structure) |
| 170 | (structure) |
| 171 | (structure) |
| 172 | (structure) |

In certain embodiments, the deuterium-enriched compound is a compound in Table 7 or a pharmaceutically acceptable salt thereof, wherein Z is H or D, provided that the abundance of deuterium in Z is at least 30% D (or at least 40%, 50%, 60%, 70%, 80%, 85%, 90%, 95%, 98%, or 99%); any H can optionally be replaced by deuterium; and the compound has a stereochemical purity of at least 75% (or at least 10%, 20%, 30%, 40%, 50%, 60%, 70%, 80%, 85%, 90%, 95%, 98%, or 99%) enantiomeric excess at the carbon atom bearing variable Z. In some embodiments, only the Z atom is enriched in deuterium.

TABLE 7

| No. | Chemical Structure |
|---|---|
| 201 | 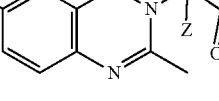 |
| 202 | 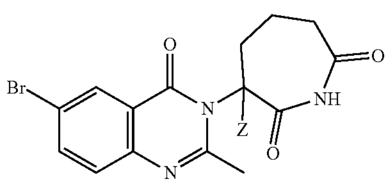 |
| 203 | 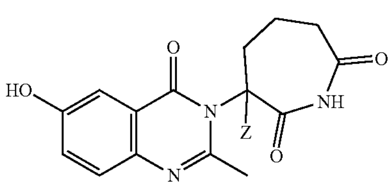 |
| 204 | 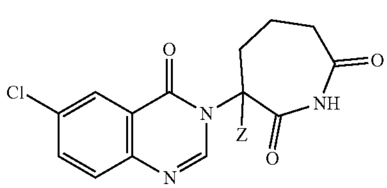 |
| 205 | 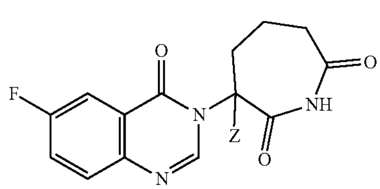 |
| 206 | 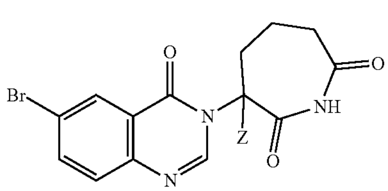 |
| 207 | 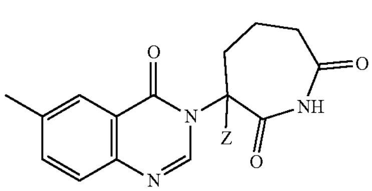 |

TABLE 7-continued

| No. | Chemical Structure |
|---|---|
| 208 | 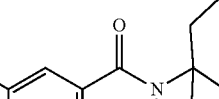 |
| 209 | 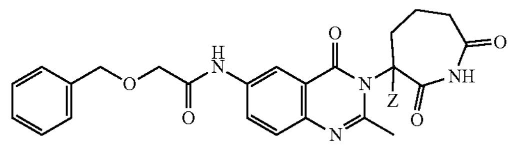 |
| 210 | 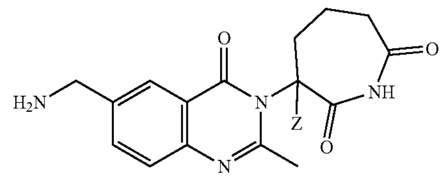 |
| 211 | 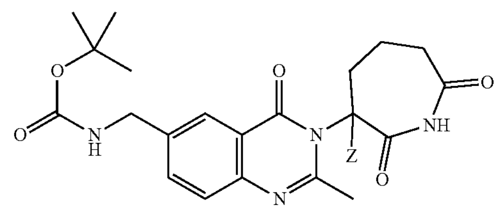 |
| 212 | 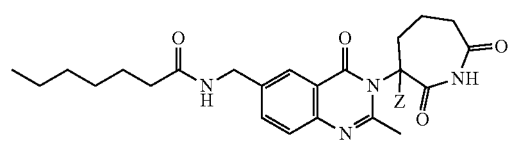 |
| 213 | 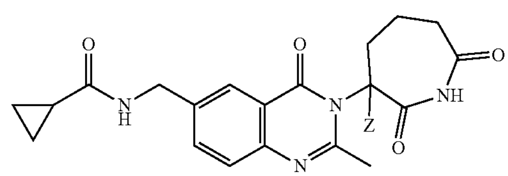 |
| 214 | 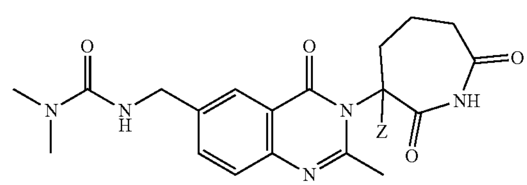 |
| 215 | 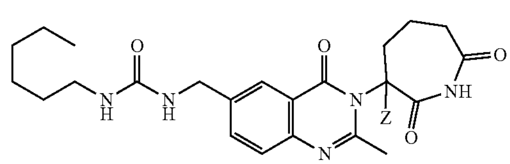 |

TABLE 7-continued

| No. | Chemical Structure |
|---|---|
| 216 | |
| 217 | |
| 218 | |
| 219 | |
| 220 | |
| 221 | |
| 222 | 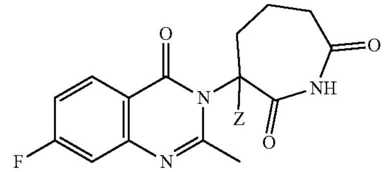 |
| 223 | 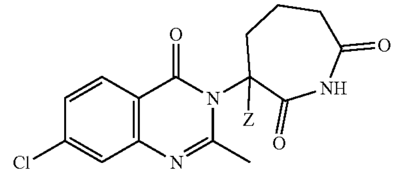 |
| 224 | 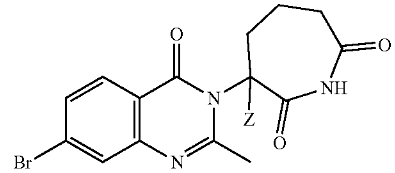 |
| 225 | 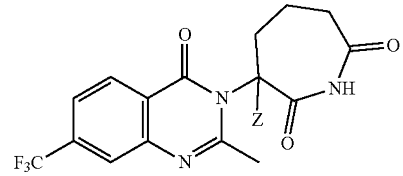 |
| 226 | 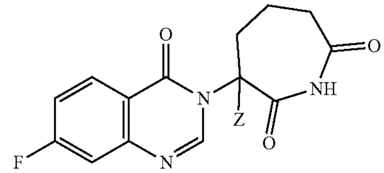 |
| 227 | 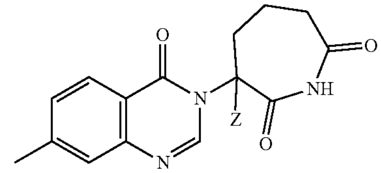 |
| 228 | 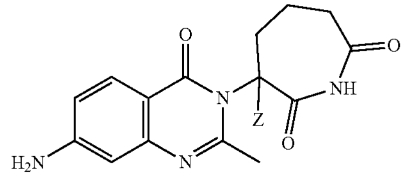 |
| 229 | 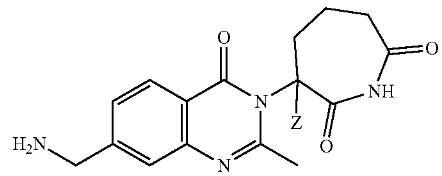 |

TABLE 7-continued

| No. | Chemical Structure |
|-----|-------------------|
| 230 | (structure) |
| 231 | (structure) |
| 232 | (structure) |
| 233 | (structure) |
| 234 | (structure) |
| 235 | (structure) |
| 236 | (structure) |
| 237 | (structure) |
| 238 | (structure) |
| 239 | (structure) |
| 240 | (structure) |

In another aspect, the invention provides a deuterium-enriched form of a compound described in WO 2016/191178, which is hereby incorporated by reference, wherein a stereogenic center having H is replaced with D. In certain embodiments, the deuterium enriched compound optionally contains one or more additional sites of deuterium enrichment in addition to the aforementioned deuterium enrichment at the stereogenic center.

In another aspect, the present invention provides a pharmaceutical composition comprising a deuterium-enriched compound described herein and a pharmaceutically acceptable carrier.

Deuterium-enriched compounds of the invention can generally be prepared by substituting a deuterium-enriched reagent for a non-isotopically labeled reagent in synthetic schemes reported in the literature for making non-isotopically labeled isoindolinonyl-azepanediones, oxoquinazolin-3(4H)-yl-azepanediones, and related compounds. Exemplary procedures for preparing the carbon-heteroatom backbone of various compounds are described in, for example, WO 2016/191178, which is hereby incorporated by reference. Additionally, deuterated 1,3-dioxoisoindolin-4-yl compounds and synthetic methods for their preparation are described, for example, in U.S. Pat. No. 9,090,585, which is hereby incorporated by reference in its entirety. Deuterated oxoquinazolin-3(4H)-yl compounds and synthetic methods for their preparation are described, for example, in U.S. Pat. Nos. 9,290,475 and 9,540,340, which are hereby incorporated by reference in their entirety. Deuterated oxo-isoindolinyl compounds and synthetic methods for their preparation are described, for example, in U.S. Pat. No. 8,288,414, which is hereby incorporated by reference in its entirety.

Schemes 1-4 below illustrate general methods for preparing deuterium-enriched isoindolinonyl-azepanediones, oxoquinazolin-3(4H)-yl-azepanediones, and related compounds enriched with deuterium at one or more positions. The schemes and description below are provided for the purpose of illustrating the invention, and should not be regarded in any manner as limiting the scope or the spirit of the invention.

As shown in Scheme 1 where variable Z is a mixture of H and D such that the abundance of deuterium in Z is at least 30%, the preparation of a deuterium-enriched isoindolinonyl-azepanedione may begin by reacting deuterium-enriched 3-aminoazepan-2-one A with benzoate ester B to form isoindolinonyl-azepanone C. Oxidation conditions may be used to convert isoindolinonyl-azepanone C to isoindolinonyl-azepanedione D.

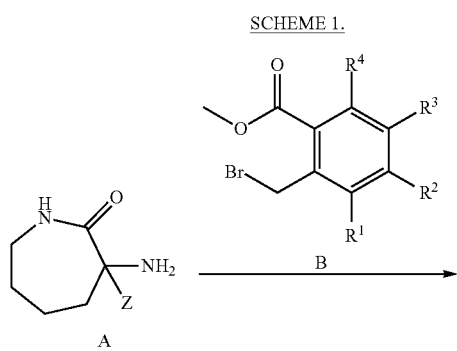

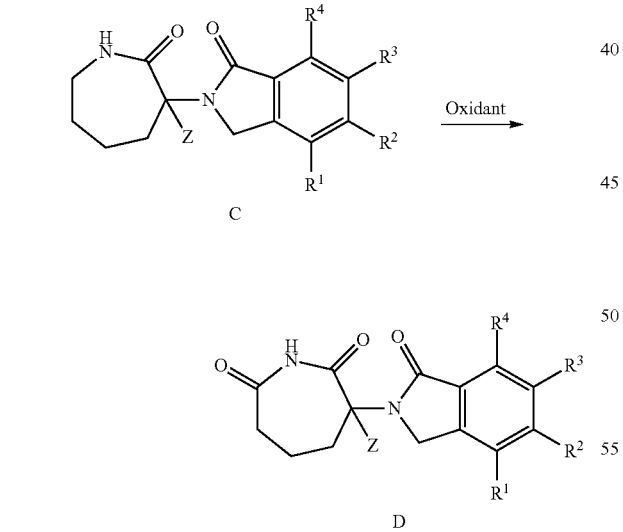

As shown in Scheme 2 where variable Z is a mixture of H and D such that the abundance of deuterium in Z is at least 30%, the preparation of a deuterium-enriched isoindolinedionyl-azepanedione may begin by reacting deuterium-enriched 3-aminoazepan-2-one A with isobenzofuran-1,3-dione E to form isoindolinedionyl-azepanone F. Oxidation conditions may be used to convert isoindolinedionyl-azepanone F to isoindolinedionyl-azepanedione G.

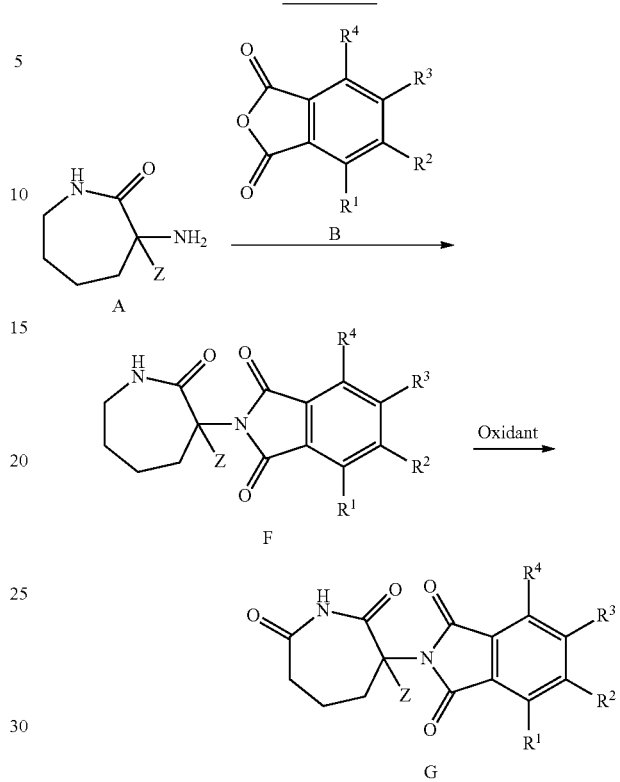

As shown in Scheme 3 where variable Z is a mixture of H and D such that the abundance of deuterium in Z is at least 30%, preparation of a deuterium-enriched oxoquinazolin-3(4H)-yl-azepanedione may begin by reacting deuterium-enriched 3-aminoazepan-2,7-dione H with aminobenzoic acid I to form amide J using amide-coupling conditions. Exemplary amide coupling conditions include those described in the literature, which may include using one or more of the following reagents in an amide coupling reaction: EDCI (1-Ethyl-3-(3-dimethylaminopropyl)carbodiimide), HOBT (hydroxybenzotriazole), or HATU (1-[Bis(dimethylamino)methylene]-1H-1,2,3-triazolo[4,5-b]pyridinium 3-oxid hexafluorophosphate). Amide J may then be converted to oxoquinazolin-3(4H)-yl-azepanedione K, for example, by exposure to, for example, triethyl orthoacetate.

SCHEME 3.

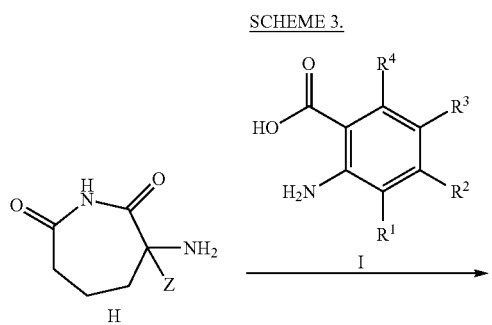

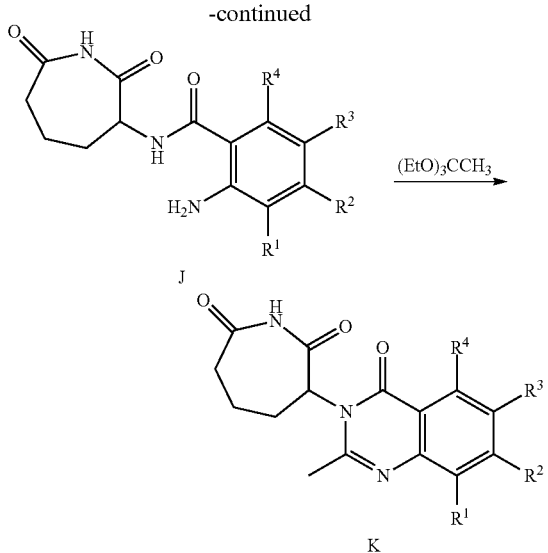

As an alternative synthetic procedure, a deuterium-enriched azepanedione may be prepared by subjecting a compound L to deuterium/hydrogen exchange, such as subjecting the compound to D2O/base conditions followed by usual workup and isolation of the deuterated compound M, as illustrated in Scheme 4 where variable Z is a mixture of H and D such that the abundance of deuterium in Z is at least 30%.

SCHEME 4.

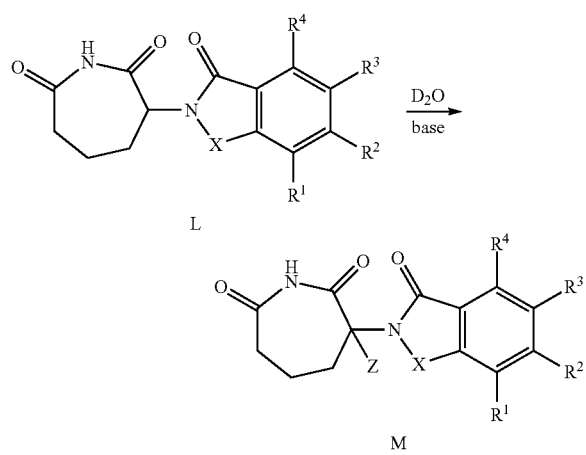

Deuterium-enriched compounds (e.g., compound M) may be used in racemic form or they may be synthesized in enantioenriched form, e.g., by employing A or H in enantioenriched form. Enantioenriched form of deuterated compounds may also be achieved by separating the R-enantiomer and S-enantiomer using chiral chromatography, such as chiral high-performance liquid chromatography. Alternatively, the R-enantiomer and S-enantiomer of M may be separated by reaction with a chiral carboxylic acid to form a salt, followed by separation of the resulting diastereomeric salts, and conversion of the separated salts back to the deuterated free base in enantiopure form.

Compounds having deuterium enrichment at a position other than those specifically mentioned above can be prepared by selecting an appropriate deuterium-enriched starting material, or by known methods of introducing a deuterium atom or exchanging a proton for a deuteron that are known in the art.

Compounds described herein can be provided in isolated or purified form. Isolated or purified compounds are a group of compounds that have been separated from their environment, such as from a crude reaction mixture if made in a laboratory setting or removed from their natural environment if naturally occurring. Examples of the purity of the isolated compound include, for example, at least 50%, 55%, 60%, 65%, 70%, 75%, 80%, 85%, 90%, 95%, to 100% by weight.

Another aspect of the invention provides a unit quantum of a deuterium-enriched compound described herein, such as an amount of at least (a) one μg of a disclosed deuterium-enriched compound, (b) one mg, or (c) one gram. In further embodiments, the quantum is, for example, at least 0.01, 0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

II. Therapeutic Applications

The invention provides methods of using deuterium-enriched compounds described herein to treat medical disorders. The deuterium-enriched compound can be, for example, a compound of Formula I, II, III, IV, V, or VI, or one of the other deuterium-enriched compounds described in Section I above. Various aspects of the invention pertaining to treating medical disorders are described below.

Accordingly, one aspect of the invention provides a method of treating a medical disorder in a patient. The method comprises administering to a patient in need thereof a therapeutically effective amount of a compound described herein, such as a deuterium-enriched compound described in Section 1 above, to treat the disorder. The disorder may be, for example, selected from the group consisting of cancer, an immune disorder, and an inflammatory disorder. In certain embodiments, the disorder is cancer (e.g., a cancer of the bladder, bone, blood, brain, breast, cervix, chest, colon, endometrium, esophagus, eye, head, kidney, liver, lymph node, lung, mouth, neck, ovary, pancreas, prostate, rectum, stomach, testis, throat, or uterus.)

Without being limited by a particular theory, compounds provided herein are expected to control angiogenesis or inhibit the production of certain cytokines. Further, compounds provided herein may be immunomodulatory and/or cytotoxic, and thus, may be useful as chemotherapeutic agents. Consequently, without being limited by a particular theory, some or all of such characteristics possessed by the compounds provided herein may render them useful in treating various diseases or disorders. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, fibrosis, arthritis and autoimmune diseases. Further examples of such diseases and conditions include, but are not limited to: diabetic retinopathy; retinopathy of prematurity; corneal graft rejection; neovascular glaucoma; retrolental fibroplasia; and proliferative vitreoretinopathy.

Still further exemplary diseases or disorders include, but are not limited to, cancer, disorders associated with angiogenesis, pain including, but not limited to, Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders (including tauopathies), CNS injury, atherosclerosis and related disorders, dysfunctional sleep and related disorders, hemoglobinopathy and related disorders (e.g., anemia), TNF-α related disorders, amyloidoses, and other various diseases and disorders.

Examples of cancer and precancerous conditions that may be treated by the present methods include, but are not limited to, those described in U.S. Pat. Nos. 6,281,230 and 5,635,517 to Muller et al., in various U.S. patent publications to Zeldis, including U.S. Patent Publication Nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Specific examples of cancer that may be treated by the present methods include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating, preventing or managing either primary or metastatic tumors.

Other specific cancers that may be treated by the present method include, but are not limited to, advanced malignancy, amyloidosis, neuroblastoma, meningioma, hemangiopericytoma, multiple brain metastases, glioblastoma multiforme, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C colorectal cancer, Dukes D colorectal cancer, unresectable colorectal carcinoma, metastatic hepatocellular carcinoma, Kaposi's sarcoma, acute myeloblastic leukemia, chronic lymphocytic leukemia (CLL), Hodgkin's lymphoma, non-Hodgkin's lymphoma, cutaneous T-cell lymphoma, cutaneous B-cell lymphoma, diffuse large B-cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressiva, hormone-refractory prostate cancer, resected high-risk soft tissue sarcoma, unresectable hepatocellular carcinoma, Waldenstrom's macroglobuline-mia, smoldering myeloma, indolent myeloma, fallopian tube cancer, androgen-independent prostate cancer, androgen-dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another aspect, the cancer is refractory or resistant to chemotherapy or radiation.

Accordingly, in certain embodiments, the cancer is an advanced malignancy, amyloidosis, neuroblastoma, meningioma, hemangiopericytoma, multiple brain metastases, glioblastoma multiforme, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C colorectal cancer, Dukes D colorectal cancer, unresectable colorectal carcinoma, metastatic hepatocellular carcinoma, Kaposi's sarcoma, acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone-refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen-independent prostate cancer, androgen-dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma. In certain other embodiments, the cancer is a cancer of the bladder, bone, blood, brain, breast, cervix, chest, colon, endometrium, esophagus, eye, head, kidney, liver, lymph node, lung, mouth, neck, ovary, pancreas, prostate, rectum, stomach, testis, throat, or uterus.

In certain embodiments, the cancer is a solid tumor or a blood-borne tumor. The solid tumor and/or blood-borne tumor may be metastatic and/or drug resistant. In certain embodiments, the cancer is myeloma or lymphoma. In certain embodiments, the solid tumor is a hepatocellular carcinoma, glioblastoma, prostate cancer, colorectal cancer, ovarian cancer, or renal cancer.

In certain embodiments, the cancer is a non-Hodgkin's lymphoma that is a diffuse large B-cell lymphoma (such as characterized as being an activated B-cell phenotype). In yet other embodiments, the cancer is a non-Hodgkin's lymphoma that is a diffuse large B-cell lymphoma characterized by the expression of one or more biomarkers overexpressed in RIVA, U2932, TMD8, or OCI-Ly10 cell lines.

In certain embodiments, the cancer is relapsed or refractory.

In another aspect, provided herein are methods of treating various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. Patent Publication No. 2006/0030594, published Feb. 9, 2006, which is incorporated in its entirety by reference.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another aspect, provided herein are methods of treating various types of lymphomas, including Non-Hodgkin's lymphoma (NHL). The term "lymphoma" refers to a heterogeneous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), follicular lymphoma, and any type of the mantle cell lymphomas that can be seen under the microscope (nodular, diffuse, blastic and mantle zone lymphoma).

Additional exemplary diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis iridis (neovascularization of the angle of the eye). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

In certain embodiments, the disorder to be treated is an immune disease or an inflammatory disease. In certain other embodiments, the disorder to be treated is systemic lupus erythematosus, scleroderma, Sjogren's syndrome, ANCA-induced vasculitis, anti-phospholipid syndrome, or myasthenia gravis. The scleroderma may be localized, systemic, limited, or diffuse scleroderma. In certain embodiments, the systemic scleroderma comprises CREST syndrome (Calcinosis, Raynaud's syndrome, esophageal dysfunction or dysmotility, sclerodactyly, telangiectasia). Scleroderma is also known as systemic sclerosis or progressive systemic sclerosis. In certain embodiments, systemic sclerosis comprises scleroderma lung disease, scleroderma renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life. In certain embodiments, limited scleroderma is limited to the hands, the face, neck, or combinations thereof. In certain embodiments, diffuse scleroderma comprises skin tightening and also occurs above the wrists (or elbows). In yet other embodiments, diffuse systemic sclerosis is sine scleroderma, comprising internal organ fibrosis, but no skin tightening; or familial progressive systemic sclerosis.

In certain embodiments, the disorder to be treated is Raynaud's disease or syndrome.

Another aspect of the invention provides a method for treating a symptom of systemic lupus erythematosus by administering to a patient suffering from systemic lupus erythematosus a deuterium-enriched compound described herein, wherein the symptom is one or more of joint pain, joint swelling, arthritis, chest pain when taking a deep breath, fatigue, fever with no other cause, general discomfort, uneasiness, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood, difficulty breathing, patchy skin color, or Raynaud's phenomenon.

Another aspect of the invention provides a method for treating a symptom of scleroderma by administering to a patient suffering from scleroderma a deuterium-enriched compound described herein, wherein the symptom is one or more of (i) gradual hardening, thickening, and tightening of the skin; (ii) skin discoloration; (iii) numbness of extremities; (iv) shiny skin; (v) small white lumps under the surface of the skin that erupt into a chalky white fluid; (vi) Raynaud's esophageal dysfunction; (vii) telangiectasia; (viii) pain and/or stiffness of the joints; (ix) swelling of the hands and feet; (x) itching of the skin; (xi) stiffening and curling of the fingers; (xii) ulcers on the outside of certain joints, such as knuckles and elbows; (xiii) digestive problems, such as heartburn, difficulty swallowing, diarrhea, irritable bowel, and constipation; (xiv) fatigue and weakness; (xv) shortness of breath; (xvi) arthritis; (xvii) hair loss; (xviii) internal organ problems; (xix) digital ulcers; and (xx) digital autoamputation.

Another aspect of the invention provides a method for improving the modified Rodnan skin score, reducing or improving the skin thickness, reducing or improving skin induration, improving the pulmonary function, improving the dermatology quality of life index, improving the carbon monoxide diffusing capacity, improving the Mahler Dyspnea index, improving the Saint George's Respiratory Questionnaire score, improving the UCLA Scleroderma Clinical Trial Consortium Gastrointestinal Tract score, improving flow-mediated dilatation, or improving or increasing the six minute walk distance of a patient having scleroderma, comprising administering to the patient an effective amount of a deuterium-enriched compound described herein.

Another aspect of the invention provides a method for modulating activity of a cell selected from the group consisting of a B cell and a T cell, comprising contacting the cell with an effective amount of a deuterium-enriched compound described herein to modulate the activity of the cell.

Another aspect of the invention provides a method for treating an immune-related disorder or a disorder selected from the group consisting of Sjogren's syndrome, ANCA-induced vasculitis, myasthenia gravis, Addison's disease, alopecia areata, ankylosing spondylitis, antiphospholipid-antibody syndrome, antiphospholipid syndrome (primary or secondary), asthma, autoimmune gastritis, autoimmune hemolytic anemia, autoimmune hepatitis, autoimmune inner-ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatrical pemphigoid (e.g., mucous membrane pemphigoid), cold agglutinin disease, Degos disease, dermatitis hepatiformis, essential mixed cryoglobulinemia, Goodpasture's syndrome, Graves' disease, Guillain-Barré syndrome, Hashimoto's thyroiditis (Hashimoto's disease; autoimmune thyroiditis), idiopathic pulmonary fibrosis, idiopathic thrombocytopenia purpura, IgA nephropathy, juvenile arthritis, lichen planus, Méniére's disease, mixed connective-tissue disease, morphea, narcolepsy, neuromyotonia, pediatric autoimmune neuropsychiatric disorders associated with streptococcal infection (PANDAs), pemphigus vulgaris, pernicious anemia, polyarteritis nodosa, polychondritis, polymyalgia rheumatica, primary agammaglobulinemia, primary biliary cirrhosis, Raynaud's disease (Raynaud's phenomenon), Reiter's syndrome, relapsing polychondritis, rheumatic fever, Sjogren's syndrome, stiff-person syndrome (Moersch-Woltmann syndrome), Takayasu's arteritis, temporal arteritis (giant cell arteritis), uveitis, vasculitis (e.g., vasculitis not associated with lupus erythematosus), vitiligo, and Wegener's granulomatosis. The method comprises administering to a patient in need thereof a therapeutically effective amount of a deuterium-enriched compound described herein to treat the disorder.

Another aspect of the invention provides a method of treating pain in a subject, comprising administering to a patient in need thereof a therapeutically effective amount of a deuterium-enriched compound described herein. Exemplary types of pain include nociceptive pain, neuropathic pain, mixed pain of nociceptive and neuropathic origin, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, complex regional pain syndrome (CRPS) type I, CRPS type II, reflex sympathetic dystrophy (RSD), reflex neurovascular dystrophy, reflex dystrophy, sympathetically maintained pain syndrome, causalgia, Sudeck's atrophy of bone, algoneurodystrophy, shoulder hand syndrome, post-traumatic dystrophy, trigeminal neuralgia, post-herpetic neuralgia, cancer-related pain, phantom-limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

Complex regional pain syndrome (CRPS) and CRPS and related syndromes mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Further types of pain contemplated for treatment include, but are not limited to, those described in U.S. Patent Publication No. 2005/0203142, published Sep. 15, 2005, which is incorporated in its entirety herein by reference.

Examples of macular degeneration (MD) and related syndromes include, but are not limited to, those described in U.S. Patent Publication No. 2004/0091455, published May 13, 2004, which is incorporated in its entirety herein by reference. Specific examples include, but are not limited to, atrophic (dry) MD, exudative (wet) MD, age-related maculopathy (ARM), choroidal neovascularisation (CNV), retinal pigment epithelium detachment (PED), and atrophy of retinal pigment epithelium (RPE).

Examples of skin diseases include, but are not limited to, those described in U.S. Patent Publication No. 2005/0214328A1, published Sep. 29, 2005, which is incorporated in its entirety herein by reference. Specific examples include, but are not limited to, keratoses and related symptoms, skin diseases or disorders characterized with overgrowths of the epidermis, acne, and wrinkles.

"Keratosis" refers to any lesion on the epidermis marked by the presence of circumscribed overgrowths of the horny layer, including but not limited to, actinic keratosis, seborrheic keratosis, keratoacanthoma, keratosis follicularis (Darier's disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratosis, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratosis, sign of Leser-Trdlat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, Cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. Patent Publication No. 2005/0239842A1, published Oct. 27, 2005, which is incorporated in its entirety herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramine, congenital heart disease, pulmonary venous hypertension, chronic obstructive pulmonary disease (COPD), interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but are not limited to, those described in U.S. Patent Publication No. 2005/0100529, published May 12, 2005, which is incorporated in its entirety herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. Patent Publication No. 2006/0154880, published Jul. 13, 2006, which is incorporated in its entirety herein by reference. Parasitic diseases include diseases and disorders caused by human intracellular parasites such as, but not limited to, *P. falciparum, P. ovale, P. vivax, P. malariae, L. donovari, L. infantum, L. aethiopica, L. major, L. tropica, L. mexicana, L. braziliensis,* T *Gondii, B. microti, B. divergens, B. coli, C. parvum, C. cayetanensis, E. histolytica, I. belli, S. mansonii, S. haematobium, Trypanosoma* spp., *Toxoplasma* spp., and *O. volvulus*. Other diseases and disorders caused by non-human intracellular parasites such as, but not limited to, *Babesia bovis, Babesia canis, Banesia gibsoni, Besnoitia darlingi, Cytauxzoon felis, Eimeria* spp., *Hammondia* spp., and *Theileria* spp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. patent application Ser. No. 11/289,723, filed Nov. 30, 2005. Specific examples include, but are not limited to, adenosine deaminase deficiency, antibody deficiency with normal or elevated Igs, ataxia-telangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wiskott-Aldrich syndrome, X-linked agammaglobulinemia, X-linked severe combined immunodeficiency.

Examples of CNS disorders include, but are not limited to, those described in U.S. Patent Publication No. 2005/0143344, published Jun. 30, 2005, which is incorporated in its entirety herein by reference. Specific examples include, but are not limited to, amyotrophic lateral sclerosis, Alzheimer's disease, Parkinson's disease, Huntington's disease, multiple sclerosis, other neuroimmunological disorders such as Tourette syndrome, delirium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. Patent Publication No. 2006/0122228, published Jun. 8, 2006, which is incorporated in its entirety herein by reference. Specific examples include, but are not limited to, CNS injury/damage and related syndromes, including, but not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete spinal cord injury (SCI), incomplete SCI, acute SCI, subacute SCI, chronic SCI, central cord syndrome, Brown-Séquard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but are not limited to, viral, genetic, allergic, and autoimmune diseases. Specific examples include, but are not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post-ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory bowel disease, multiple sclerosis, systemic lupus erythematosus, erythema nodosum leprosum (ENL) in leprosy, radiation damage, cancer, asthma, or hyperoxic alveolar injury.

Examples of atherosclerosis and related conditions include, but are not limited to, those disclosed in U.S. Patent Publication No. 2002/0054899, published May 9, 2002, which is incorporated in its entirety herein by reference. Specific examples include, but are not limited to, all forms of conditions involving atherosclerosis, including restenosis after vascular intervention such as angioplasty, stenting, atherectomy and grafting. All forms of vascular intervention are contemplated herein, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary bypass grafting, angioplasty with stent implantation, peripheral percutaneous transluminal intervention of the iliac, femoral or popliteal arteries, and surgical intervention using impregnated artificial grafts.

Exemplary major systemic arteries that may be in need of treatment, include, for example, Axillary, Brachial, Brachiocephalic, Celiac, Common carotid, Common iliac, Coronary, Deep femoral, Digital, Dorsalis pedis, External carotid, External iliac, Femoral, Gastric, Hepatic, Inferior mesenteric, Internal carotid, Internal iliac, Left gastric, Middle sacral, Ovarian, Palmar arch, Peroneal, Popliteal, Posterior tibial, Pulmonary, Radial, Renal, Splenic, Subclavian, Superior mesenteric, Testicular, and Ulnar.

Examples of dysfunctional sleep and related syndromes include, but are not limited to, those disclosed in U.S. Patent Publication No. 2005/0222209A1, published Oct. 6, 2005, which is incorporated in its entirety herein by reference. Specific examples include, but are not limited to, snoring, sleep apnea, insomnia, narcolepsy, restless leg syndrome, sleep terrors, sleep walking, sleep eating, and dysfunctional sleep associated with chronic neurological or inflammatory conditions. Chronic neurological or inflammatory conditions, include, but are not limited to, complex regional pain syndrome (CRPS), chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, postherpetic, traumatic or inflammatory), and neurodegenerative disorders such as Parkinson's disease, Alzheimer's disease, amyotrophic lateral sclerosis (ALS), multiple sclerosis, Huntington's disease, bradykinesia, muscle rigidity, parkinsonian tremor, parkinsonian gait, motion freezing, depression, defective long-term memory, Rubinstein-Taybi syndrome (RTS), dementia, postural instability, hypokinetic disorders, synuclein disorders, multiple system atrophies, striatonigral degeneration, olivopontocerebellar atrophy, Shy-Drager syndrome, motor neuron disease with parkinsonian features, Lewy body dementia, Tau pathology disorders, progressive supranuclear palsy, corticobasal degeneration, frontotemporal dementia, amyloid pathology disorders, mild cognitive impairment, Alzheimer's disease with parkinsonism, Wilson disease, Hallervorden-Spatz disease, Chédiak-Higashi disease, SCA-3 spinocerebellar ataxia, X-linked dystonia parkinsonism, prion disease, hyperkinetic disorders, chorea, ballismus, dystonia tremors, CNS trauma, and myoclonus.

Examples of hemoglobinopathy and related disorders include, but are not limited to, those described in U.S. Patent Publication No. 2005/0143420A1, published Jun. 30, 2005, which is incorporated in its entirety herein by reference. Specific examples include, but are not limited to, hemoglobinopathy, sickle cell anemia, and any other disorders related to the differentiation of CD34+ cells.

Examples of TNF-α related disorders include, but are not limited to, those described in WO 2014/004990, WO 98/03502, and WO 98/54170, all of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; graft versus host reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis, psoriatic arthritis and other arthritic conditions, septic shock, sepsis, endotoxic shock, graft versus host disease, wasting, ulcerative colitis, multiple sclerosis, systemic lupus erythematosus, ENL in leprosy, HIV, AIDS, and opportunistic infections in AIDS; disorders such as endotoxic shock, hemodynamic shock and sepsis syndrome, post-ischemic reperfusion injury, malaria, mycobacterial infection, meningitis, psoriasis, congestive heart failure, fibrotic disease, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In other aspects, the use of compounds provided herein in various immunological applications, in particular, as vaccine adjuvants, particularly anticancer vaccine adjuvants, as disclosed in U.S. Patent Publication No. 2007/0048327, which is incorporated herein in its entirety by reference, is also encompassed. These embodiments also relate to the uses of compounds provided herein in combination with vaccines to treat or prevent cancer or infectious diseases, and other various uses of immunomodulatory compounds such as reduction or desensitization of allergic reactions.

Additional medical disorders for treatment include those described in international patent application publication nos. WO 2012/125459 and WO 2012/125475, each of which is hereby incorporated by reference.

In one aspect, the invention provides a method for treating a disorder selected from the group consisting of angiogenesis and a cytokine-related disorder, comprising administering to a patient in need thereof a therapeutically effective amount of a deuterium-enriched isoindolinonyl-azepanedione, a deuterium-enriched oxoquinazolin-3(4H)-yl-azepanedione, or a related compound described herein to treat the disorder.

In one aspect, the invention provides a method of treating cancer in a patient, comprising administering to a patient in need thereof a therapeutically effective amount of a deuterium-enriched isoindolinonyl-azepanedione, a deuterium-enriched oxoquinazolin-3(4H)-yl-azepanedione, or a related compound described herein to treat the cancer.

In certain embodiments, the cancer is a cancer of the bladder, bone, blood, brain, breast, cervix, chest, colon, endometrium, esophagus, eye, head, kidney, liver, lymph node, lung, mouth, neck, ovary, pancreas, prostate, rectum, stomach, testis, throat, or uterus.

In certain embodiments, the cancer is an advanced malignancy, amyloidosis, neuroblastoma, meningioma, hemangiopericytoma, multiple brain metastases, glioblastoma multiforme, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C colorectal cancer, Dukes D colorectal cancer, unresectable colorectal carcinoma, metastatic hepatocellular carcinoma, Kaposi's sarcoma, acute myeloblastic leukemia, Hodgkin's lymphoma, non-Hodgkin's lymphoma, cutaneous T-cell lymphoma, cutaneous B-cell lymphoma, diffuse large B-cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressiva, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen-independent prostate cancer, androgen-dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In one aspect, the invention provides a method of treating a disorder selected from the group consisting of an immune disorder and an inflammatory disorder, comprising administering to a patient in need thereof a therapeutically effective amount of a deuterium-enriched isoindolinonyl-azepanedione, a deuterium-enriched oxoquinazolin-3(4H)-yl-azepanedione, or a related compound described herein to treat the disorder.

In certain embodiments, the disorder is Sjogren's syndrome, ANCA-induced vasculitis, Addison's disease, alopecia areata, ankylosing spondylitis, antiphospholipid antibody syndrome, antiphospholipid syndrome, asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatricial pemphigoid, cold agglutinin disease, Degos disease, dermatitis hepatiformis, essential mixed cryoglobulinemia, Goodpasture's syndrome, Graves' disease, Guillain-Barré syndrome, Hashimoto's thyroiditis, idiopathic pulmonary fibrosis, idiopathic thrombocytopenia purpura, IgA nephropathy, juvenile arthritis, lichen planus, Méniére's disease, mixed connective tissue disease, morphea, narcolepsy, neuromyotonia, a pediatric autoimmune neuropsychiatric disorder, pemphigus vulgaris, pernicious anemia, polyarteritis *nodosa*, polychondritis, polymyalgia rheumatica, primary agammaglobulinemia, primary biliary cirrhosis, Raynaud's disease, Reiter's syndrome, relapsing polychondritis, rheumatic fever, stiff-person syndrome, Takayasu's arteritis, temporal arteritis, uveitis, vasculitis, vitiligo, or Wegener's granulomatosis.

In certain embodiments, the disorder is systemic lupus erythematosus, scleroderma, Sjogren's syndrome, ANCA-induced vasculitis, anti-phospholipid syndrome, or myasthenia gravis.

Additional disorders and methods of treatment are disclosed in U.S. Pat. No. 8,518,972, U.S. Patent Publication Nos. 2013/0324518 and 2015/0119435, and international patent application publications WO 2011/100380 and WO 2014/004990; all of which are hereby incorporated by reference in their entireties.

In one aspect, the present invention provides a method of treating a disorder selected from the group consisting of cancer, an immune disorder, and an inflammatory disorder, comprising administering to a patient in need thereof a therapeutically effective amount of a deuterium-enriched compound described herein (such as a deuterium-enriched isoindolinonyl-azepanedione, deuterium-enriched oxoquinazolin-3(4H)-yl-azepanedione, or related compound) to treat the disorder.

In certain embodiments, the disorder is cancer. In certain embodiments, the cancer is a cancer of the bladder, bone, blood, brain, breast, cervix, chest, colon, endometrium, esophagus, eye, head, kidney, liver, lymph node, lung, mouth, neck, ovary, pancreas, prostate, rectum, stomach, testis, throat, or uterus. In certain embodiments, the cancer is an advanced malignancy, amyloidosis, neuroblastoma, meningioma, hemangiopericytoma, multiple brain metastases, glioblastoma multiforme, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C colorectal cancer, Dukes D colorectal cancer, unresectable colorectal carcinoma, metastatic hepatocellular carcinoma, Kaposi's sarcoma, acute myeloblastic leukemia, Hodgkin's lymphoma, non-Hodgkin's lymphoma, cutaneous T-cell lymphoma, cutaneous B-cell lymphoma, diffuse large B-cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressiva, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen-independent prostate cancer, androgen-dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

In certain embodiments, the disorder is an immune disorder.

In certain embodiments, the disorder is an inflammatory disorder.

In certain embodiments, the disorder is Sjogren's syndrome, ANCA-induced vasculitis, Addison's disease, alopecia areata, ankylosing spondylitis, antiphospholipid antibody syndrome, antiphospholipid syndrome, asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatricial pemphigoid, cold agglutinin disease, Degos disease, dermatitis hepatiformis, essential mixed cryoglobulinemia, Goodpasture's syndrome, Graves' disease, Guillain-Barré syndrome, Hashimoto's thyroiditis, idiopathic pulmonary fibrosis, idiopathic thrombocytopenia purpura, IgA nephropathy, juvenile arthritis, lichen planus, Méniére's disease, mixed connective tissue disease, morphea, narcolepsy, neuromyotonia, a pediatric autoimmune neuropsychiatric disorder, pemphigus vulgaris, pernicious anemia, polyarteritis *nodosa*, polychondritis, polymyalgia rheumatica, primary agammaglobulinemia, primary biliary cirrhosis, Raynaud's disease, Reiter's syndrome, relapsing polychondritis, rheumatic fever, stiff-person syndrome, Takayasu's arteritis, temporal arteritis, uveitis, vasculitis, vitiligo, or Wegener's granulomatosis.

In certain embodiments, the disorder is systemic lupus erythematosus, scleroderma, Sjogren's syndrome, ANCA-induced vasculitis, anti-phospholipid syndrome, or myasthenia gravis.

Still other collections of medical disorders for treatment include asthma, autoimmune diseases, cancers, ciliopathies, cleft palate, diabetes, heart disease, hypertension, inflammatory bowel disease, mental retardation, mood disorder, obesity, refractive error, infertility, Angelman syndrome, celiac disease, Charcot-Marie-Tooth disease, cystic fibrosis, Duchenne muscular dystrophy, hemochromatosis, hemophilia, Klinefelter's syndrome, neurofibromatosis, phenylketonuria, polycystic kidney disease, (PKD1 or PKD2), Prader-Willi syndrome, sickle-cell disease, Tay-Sachs disease, Turner syndrome, Alzheimer's disease, amyotrophic lateral sclerosis (Lou Gehrig's disease), anorexia nervosa, anxiety disorder, atherosclerosis, attention deficit hyperactivity disorder, autism, bipolar disorder, chronic fatigue syndrome, chronic obstructive pulmonary disease, Crohn's disease, coronary heart disease, dementia, depression, diabetes mellitus type 1, diabetes mellitus type 2, epilepsy. Guillain-Barre syndrome, irritable bowel syndrome, lupus, metabolic syndrome, multiple sclerosis, myocardial infarction, obesity, obsessive-compulsive disorder, panic disorder, Parkinson's disease, psoriasis, rheumatoid arthritis, sarcoidosis, schizophrenia, stroke, thromboangiitis obliterans, Tourette syndrome, vasculitis, aceruloplasminemia, achondrogenesis type II, achondroplasia, acrocephaly. Gaucher disease type 2, acute intermittent porphyria, Canavan disease, adenomatous Polyposis Coli, ALA dehydratase deficiency, adenylosuccinate lyase deficiency, adrenogenital syndrome, adrenoleukodystrophy, ALA-D porphyria, alkaptonuria, Alexander disease, alkaptonuric ochronosis, alpha-1 antitrypsin deficiency, alpha-1 proteinase inhibitor, emphysema, amyotrophic lateral sclerosis, Alstrom syndrome, amelogenesis imperfecta, Anderson-Fabry disease, androgen insensitivity syndrome, anemia, angiokeratoma corporis diffusum, angiomatosis retinae (von Hippel-Lindau disease), Apert syndrome, arachnodactyly (Marfan syndrome), Stickler syndrome, arthrochalasis multiplex congenital (Ehlers-Danlos syndrome, arthrochalasia type), ataxia telangiectasia, Rett syndrome, primary pulmonary hypertension, Sandhoff disease, neurofibromatosis type II, Beare-Stevenson cutis gyrata syndrome, Mediterranean fever, familial Benjamin syndrome, beta-thalassemia, bilateral acoustic neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dube syndrome, brittle bone disease (osteogenesis imperfecta), Rubinstein-Taybi syndrome, bronze diabetes/bronzed cirrhosis (hemochromatosis), bulbospinal muscular atrophy (Kennedy's disease), Burger-Grutz syndrome (lipoprotein lipase deficiency), CGD chronic granulomatous disorder, campomelic dysplasia, biotinidase deficiency, cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, chondrodystrophy syndrome (achondroplasia), otospondylomegaepiphyseal dysplasia, Lesch-Nyhan syndrome, galactosemia, Ehlers-Danlos syndrome, thanatophoric dysplasia, Coffin-Lowry syndrome, Cockayne syndrome (familial adenomatous polyposis), congenital erythropoietic porphyria, congenital heart disease, methemoglobinemia/congenital methemoglobinaemia, achondroplasia, connective tissue disease, conotruncal anomaly face syndrome, Cooley's anemia (beta-thalassemia), copper storage disease (Wilson's disease), copper transport disease (Menkes disease), hereditary coproporphyria, Cowden syndrome, craniofacial dysarthrosis (Crouzon syndrome), Creutzfeldt-Jakob disease (prion disease), Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy Duchenne and Becker types (DBMD), Usher syndrome, degenerative nerve diseases including de Grouchy syndrome and Dejerine-Sottas syndrome, developmental disabilities, distal spinal muscular atrophy, type V, androgen insensitivity syndrome, diffuse globoid body sclerosis (Krabbe disease), Di George's syndrome, dihydrotestosterone receptor deficiency, androgen insensitivity syndrome, Down syndrome, dwarfism, erythropoietic protoporphyria, erythroid 5-aminolevulinate synthetase deficiency, erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), fibrocystic disease of the pancreas, fragile X syndrome, galactosemia, genetic brain disorders, giant cell hepatitis (neonatal hemochromatosis), Gronblad-Strandberg syndrome (pseudoxanthoma elasticum), Gunther disease (congenital erythropoietic porphyria), Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), hyperandrogenism, hypochondroplasia, hypochromic anemia, immune system disorders, Insley-Astley syndrome, Jackson-Weiss syndrome, Joubert syndrome, Lesch-Nyhan syndrome, kidney diseases, including hyperoxaluria, Klinefelter's syndrome, Kniest dysplasia, lacunar dementia, Langer-Saldino achondrogenesis, ataxia telangiectasia, Lynch syndrome, lysyl-hydroxylase deficiency, Machado-Joseph disease, metabolic disorders, movement disorders, Mowat-Wilson syndrome, Muenke syndrome, multiple neurofibromatosis, Nance-Insley syndrome, Nance-Sweeney chondrodysplasia, Niemmam-Pick disease, Noack syndrome (Pfeiffer syndrome), Osler-Weber-Rendu disease, Peutz-Jeghers syndrome, polyostotic fibrous dysplasia (McCune-Albright syndrome), Peutz-Jeghers syndrome, Prader-Labhart-Willi syndrome, primary pulmonary hypertension, primary senile degenerative dementia, prion disease, progeria (Hutchinson-Gilford progeria syndrome), progressive chorea, progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), recurrent polyserositis, retinal disorders, retinoblastoma, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita), SEMD, Strudwick type (spondyloepimetaphyseal dysplasia, Strudwick type), Shprintzen syndrome, skin pigmentation disorders, Smith-Lemli-Opitz syndrome, South-African genetic porphyria (variegate porphyria), infantile-onset ascending hereditary spastic paralysis, speech and communication disorders, sphingolipidosis, spinocerebellar ataxia, Stickler syndrome, stroke, androgen insensitivity syndrome, tetrahydrobiopterin deficiency, beta-thalassemia, thyroid disease, tomaculous neuropathy (hereditary neuropathy with liability to pressure palsies), Treacher-Collins syndrome, triplo X syndrome (triple X syndrome), trisomy 21 (Down syndrome), trisomy X, VHL syndrome (von Hippel-Lindau disease), vision impairment and blindness (Alstrom syndrome), Vrolik disease, Waardenburg syndrome, Warburg-Sjo-Fledelius syndrome, Weissenbacher-Zweymuller syndrome, Wolf-Hirschhom syndrome, Wolff periodic disease, or Xerodenna pigmentosum. In certain embodiments, the disorder for treatment is a cancer (e.g., a squamous-cell carcinoma, basal cell carcinoma, adenocarcinoma, hepatocellular carcinomas, renal cell carcinomas; cancer of the bladder, bowel, breast, cervix, colon, esophagus, head, kidney, liver, lung, neck, ovary, pancreas, prostate, and stomach; a leukemia; a benign or malignant lymphoma; a benign or malignant melanoma; a myeloproliferative disease; a sarcoma; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor, or a teratocarcinoma).

Another aspect of the invention provides a method of treating or preventing a disease characterized by oxidative stress. The method comprises administering to a patient in need thereof a deuterium-enriched compound described herein to treat or prevent the disease characterized by oxidative stress. Exemplary diseases characterized by oxidative stress include, for example, cancer, a hyperproliferative cell growth condition, Parkinson's disease, Alzheimer's disease, atherosclerosis, heart failure (including congestive heart failure), myocardial infarction, schizophrenia, bipolar disorder, fragile X syndrome, sickle cell disease, chronic fatigue syndrome, aging (including aging by induction of mitohormesis), diabetes (e.g., type I diabetes) and vascular disease.

Dosages

Doses of a compound provided herein, or a pharmaceutically acceptable salt, solvate, or stereoisomer thereof, vary depending on factors such as: specific indication to be treated; age and condition of a patient; and amount of second active agent used, if any. Generally, a compound provided herein, or a pharmaceutically acceptable salt, solvate, or stereoisomer thereof, may be used in an amount of from about 0.1 mg to about 500 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

Second Active Agents

A compound provided herein, or a pharmaceutically acceptable salt, solvate, or stereoisomer thereof, can be combined with other pharmacologically active compounds ("second active agents") in methods and compositions provided herein. Certain combinations may work synergistically in the treatment of particular types of diseases or disorders, and conditions and symptoms associated with such diseases or disorders. A compound provided herein, or a pharmaceutically acceptable salt, solvate, or stereoisomer thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransferase inhibitors; IkB kinase inhibitors; p38MAPK inhibitors; EGFR inhibitors (such as, for example, gefitinib and erlotinib HCl); HER-2 antibodies (such as, for example, trastuzumab (Herceptin®) and pertuzumab (Perjeta®)); anti-PD-1 antibodies and anti-PD-L1 antibodies (such as, for example, pembrolizumab); VEGFR antibodies (such as, for example, bevacizumab (Avastin®)); VEGFR inhibitors (such as, for example, Flk-1 specific kinase inhibitors, SU5416 and PTK787/ZK222584); PI3K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies.

Examples of small molecule active agents include, but are not limited to, anticancer agents and antibiotics (e.g., clarithromycin).

Specific second active compounds that can be combined with compounds provided herein vary depending on the specific indication to be treated.

For instance, for the treatment of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; albomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozotocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25-dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogens; antiestrogens; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta-lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxyamidotriazole; cartilage-derived angiogenesis inhibitor; carzelesin; casein kinase inhibitors; castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin-816; crisnatol; cryptophycin-8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorubicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalichondrin B; itasetron; jasplakinolide; kahalalide F; lamellarin N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; fibroblast growth factor-saporin mitotoxin; mitoxantrone; mofarotene; molgramostim; Erbitux, human chorionic gonadotropin; monophosphoryl lipid A+myobacterium cell wall skeleton; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; Nitrullyn; oblimersen (Genasense®); 06-benzylguanine; octreotide; okicenone; oligonucleotides; onapristone; ondansetron; ondansetron hydrochloride; oracin; oral cytokine inducer; ormaplatin; osaterone; oxaliplatin; oxaunomycin; paclitaxel; paclitaxel analogues; paclitaxel derivatives; palau'amine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; microalgal protein kinase C inhibitors; protein tyrosine phosphatase inhibitors; purine nucleoside phosphorylase inhibitors; purpurins; pyrazoloacridine; pyridoxylated hemoglobin polyoxyethylene conjugate; Raf antagonists; raltitrexed; ramosetron; Ras farnesyl protein transferase inhibitors; Ras inhibitors; Ras-GAP inhibitor; demethylated retelliptine; rhenium-186 etidronate; rhizoxin; ribozymes; RII retinamide; rohitukine; romurtide; roquinimex; rubiginone B1; ruboxyl; safingol; saintopin; SarCNU; sarcophytol A; sargramostim; SDI-1 mimetics; semustine; senescence derived inhibitor 1; sense oligonucleotides; signal transduction inhibitors; sizofuran; sobuzoxane; sodium borocaptate; sodium phenylacetate; solverol; somatomedin-binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb(2H); and zinostatin stimalamer.

Specific second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatin, temozolomide (Temodar®), cyclophosphamide, carboplatin, procarbazine, Gliadel®, tamoxifen, topotecan, methotrexate, Taxol®, taxotere, fluorouracil, leucovorin, irinotecan, Xeloda®, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, pamitronate, Biaxin®, busulfan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In another aspect, examples of specific second agents according to the indications to be treated can be found in the following references, all of which are incorporated herein in their entireties: U.S. Pat. Nos. 6,281,230 and 5,635,517; U.S. Patent Publication Nos. 2004/0220144, 2004/0087546, 2005/0203142, 2004/0091455, 2005/0100529, 2005/0214328, 2005/0239842, 2006/0154880, 2006/0122228, 2005/0143344, and 2006/0188475.

Examples of second active agents that may be used for the treatment of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, COX-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the Physician's Desk Reference 2003. Specific examples include, but are not limited to, salicylic acid acetate (Aspirin®), celecoxib (Celebrex®), Enbrel®, ketamine, gabapentin (Neurontin®), phenytoin (Dilantin®), carbamazepine (Tegretol®), oxcarbazepine (Trileptal®), valproic acid (Depakene®), morphine sulfate, hydromorphone, prednisone, griseofulvin, penthonium, alendronate, diphenhydramine, guanethidine, ketorolac (Acular®), thyrocalcitonin, dimethylsulfoxide (DMSO), clonidine (Catapres®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine, and phenoxybenzamine.

Examples of second active agents that may be used for the treatment of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2-alpha, pentoxifylline, tin etiopurpurin, lucentis, lutetium chelates such as motexafin lutetium, 9-fluoro-11,21-dihydroxy-16,17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal-genistin, 6'-O—Ac-genistin, daidzein, daidzin, 6'-O-Mal-daidzin, 6'-O—Ac-daidzin, glycitein, glycitin, 6'-O-Mal-glycitin, biochanin A, formononetin (U.S. Pat. No. 6,001,368), triamcinolone acetonide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neutrotrophic factor (BDNF), plasminogen activator factor type 2 (PAI-2), EYE101 (Eyetech Pharmaceuticals), LY333531 (Eli Lilly), Miravant SnET2, and Retisert™ implant (Bausch & Lomb). All of the references cited herein are incorporated in their entireties by reference.

Examples of second active agents that may be used for the treatment of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen®, AlloDerm®, Cymetra®, Autologen®, Zyderm®, Zyplast®, Resoplast®, and Isolagen®.

Examples of second active agents that may be used for the treatment of pulmonary hypertension and related disorders include, but are not limited to, anticoagulants, diuretics, cardiac glycosides, calcium-channel blockers, vasodilators, prostacyclin analogues, endothelin antagonists, phosphodiesterase inhibitors (e.g., PDE V inhibitors), endopeptidase inhibitors, lipid-lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin 12 (PGI2)), epoprostenol (EPO, Floran®), treprostinil (Remodulin®), nitric oxide (NO), bosentan (Tracleer®), amlodipine, prostacyclin, tadalafil (Cialis®), simvastatin (Zocor®), omapatrilat (Vanlev®), irbesartan (Avapro®), pravastatin (Pravachol®), digoxin, L-arginine, iloprost, beraprost, and sildenafil (Viagra®).

Examples of second active agents that may be used for the treatment of asbestos-related disorders include, but are not limited to, anthracycline, platinum, alkylating agents, oblimersen (Genasense®), cyclophosphamide, Temodar®, carboplatin, procarbazine, Gliadel®, tamoxifen, topotecan, methotrexate, taxotere, irinotecan, capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, pamidronate, Biaxin®, busulfan, prednisone, bisphosphonate, arsenic trioxide, vincristine, doxorubicin (Doxil®), ganciclovir, adriamycin, bleomycin, hyaluronidase, mitomycin C, mepacrine, thiotepa, tetracycline and gemcitabine.

Examples of second active agents that may be used for the treatment of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stibogluconate), interferon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levamisole and isoprinosine; biologics such as, but not limited to, gammaglobulin, transfer factor, interleukins, and interferons; hormones such as, but not limited to, thymic hormones; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment of CNS disorders include, but are not limited to: opioids; a dopamine agonist or antagonist, such as, but are not limited to, Levodopa, L-DOPA, cocaine, α-methyltyrosine, reserpine, tetrabenazine, benzatropine, pargyline, fenoldopam mesylate, cabergoline, pramipexole dihydrochloride, ropinirole, amantadine hydrochloride (Symmetrel®), selegiline hydrochloride, carbidopa, pergolide mesylate, Sinemet® CR; a MAO inhibitor, such as, but not limited to, iproniazid, clorgiline, phenelzine and isocarboxazid; a COMT inhibitor, such as, but not limited to, tolcapone and entacapone; a cholinesterase inhibitor, such as, but not limited to, physostigmine salicylate, physostigmine sulfate, physostigmine bromide, neostigmine bromide, neostigmine methylsulfate, ambenonium chloride, edrophonium chloride, tacrine, pralidoxime chloride, obidoxime chloride, trimedoxime bromide, diacetyl monoxime, pyridostigmine, and demecarium bromide; an anti-inflammatory agent, such as, but not limited to, naproxen sodium, diclofenac sodium, diclofenac potassium, celecoxib, oxaprozin, diflunisal, etodolac, meloxicam, ibuprofen, ketoprofen, nabumetone, rofecoxib, methotrexate, leflunomide, sulfasalazine, gold salts, Rho-D Immune Globulin, mycophenolate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbiprofen, oxaprozin, piroxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopramide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, pipamazine, scopolamine, sulpiride, tetrahydrocannabinol, thiethylperazine, thioproperazine, tropisetron, and a mixture thereof.

Examples of second active agents that may be used for the treatment of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, ibuprofen, ketoprofen, nabumetone, rofecoxib, methotrexate, leflunomide, sulfasalazine, gold salts, Rho-D Immune Globulin, mycophenolate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, mefenamic acid, meclofenamate sodium, tolmetin, ketorolac, dichlofenac, flurbiprofen, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, colchicine, allopurinol, probenecid, sulfinpyrazone and benzbromarone; a cAMP analog including, but not limited to, db-cAMP; an agent comprising a methylphenidate drug, which comprises l-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levetiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin®, oxycontin, morphine, topiramate, amitryptiline, nortryptiline, carbamazepine, Levodopa, L-DOPA, cocaine, α-methyltyrosine, reserpine, tetrabenazine, benzatropine, pargyline, fenoldopam mesylate, cabergoline, pramipexole dihydrochloride, ropinirole, amantadine hydrochloride (Symmetrel®), selegiline hydrochloride, carbidopa, pergolide mesylate, Sinemet® CR, iproniazid, clorgiline, phenelzine, isocarboxazid, tolcapone, entacapone, physostigmine salicylate, physostigmine sulfate, physostigmine bromide, neostigmine bromide, neostigmine methylsulfate, ambenonium chloride, edrophonium chloride, tacrine, pralidoxime chloride, obidoxime chloride, trimedoxime bromide, diacetyl monoxime, pyridostigmine, demecarium bromide, naproxen sodium, diclofenac sodium, diclofenac potassium, celecoxib, sulindac, oxaprozin, diflunisal, etodolac, ibuprofen, ketoprofen, nabumetone, refecoxib, methotrexate, leflunomide, sulfasalazine, gold salts, Rho-D Immune Globulin, mycophenolate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, mefenamic acid, meclofenamate sodium, tolmetin, ketorolac, dichlofenac, flurbiprofen, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, colchicine, allopurinol, probenecid, sulfinpyrazone, benzbromarone, betamethasone and other glucocorticoids, metoclopramide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, pipamazine, scopolamine, sulpiride, tetrahydrocannabinol, thiethylperazine, thioproperazine, tropisetron, and a mixture thereof.

Examples of second active agents that may be used for the treatment of hemoglobinopathy and related disorders include, but are not limited to: interleukins, such as IL-2 (including recombinant IL-2 ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrate or butyrate derivatives; nitrous oxide; hydroxyurea; Nicosan (see U.S. Pat. No. 5,800,819); Gardos channel antagonists such as clotrimazole and triaryl methane derivatives; deferoxamine; protein C; and transfusions of blood, or of a blood substitute such as Hemospan® or Hemospan® PS (Sangart).

Administration of a compound provided herein, or a pharmaceutically acceptable salt, solvate, or stereoisomer thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One route of administration for compounds provided herein is oral. Routes of administration for the second active agents or ingredients are known to those of ordinary skill in the art. See, e.g., Physicians' Desk Reference ($60^{th}$ Ed., 2006).

In another aspect, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated, the severity and stage of disease, and the amount(s) of compounds provided herein and any optional additional active agents concurrently administered to the patient.

As discussed elsewhere herein, also encompassed is a method of reducing, treating and/or preventing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

Cycling Therapy

In certain aspects, the prophylactic or therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in another aspect, a compound provided herein is administered daily in a single or divided dose in a four to six week cycle with a rest period of about a week or two weeks. Cycling therapy further allows the frequency, number, and length of dosing cycles to be increased. Thus, another aspect encompasses the administration of a compound provided herein for more cycles than are typical when it is administered alone. In yet another aspect, a compound provided herein is administered for a greater number of cycles than would typically cause dose-limiting toxicity in a patient to whom a second active ingredient is not also being administered.

In another aspect, a compound provided herein is administered daily and continuously for three or four weeks at a dose of from about 0.1 mg to about 500 mg per day, followed by a rest of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In another aspect, a compound provided herein and a second active ingredient are administered orally, with administration of the compound provided herein occurring 30 to 60 minutes prior to the second active ingredient, during a cycle of four to six weeks. In another aspect, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

The invention may be embodied in other specific forms without departing from the spirit or essential attributes thereof. This invention encompasses all combinations of preferred aspects of the invention noted herein. It is understood that any and all aspects of the invention may be taken in conjunction with any other aspect or aspects to describe additional aspects. It is also to be understood that each individual element of the aspects is intended to be taken individually as its own independent aspect. Furthermore, any element of an aspect is meant to be combined with any and all other elements from any aspect to describe an additional aspect.

Manufacture of Medicaments

Another aspect of the invention provides for the use of a deuterium-enriched compound described herein for the manufacture of a medicament. The medicament may be for treating one or more of the medical disorders described herein, such as cancer.

III. Dosing Considerations and Combination Therapy

Doses of a compound provided herein, or a pharmaceutically acceptable salt thereof, vary depending on factors such as: specific indication to be treated; age and condition of a patient; and amount of second active agent used, if any. Generally, a compound provided herein, or a pharmaceutically acceptable salt thereof, may be used in an amount of from about 0.1 mg to about 1 g per day, or from about 0.1 mg to about 500 mg per day, and can be adjusted in a conventional fashion (e.g., the same amount administered each day of the treatment), in cycles (e.g., one week on, one week off), or in an amount that increases or decreases over the course of treatment. In other embodiments, the dose can be from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg.

In certain aspects, the therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies. These regimens can avoid or reduce the side effects of one of the therapies, and/or improve the efficacy of the treatment.

Consequently, in another aspect, a compound provided herein is administered daily in a single or divided doses in a four to six week cycle with a rest period of about a week or two weeks. Cycling therapy further allows the frequency, number, and length of dosing cycles to be increased. Thus, another aspect encompasses the administration of a compound provided herein for more cycles than are typical when it is administered alone. In yet another aspect, a compound provided herein is administered for a greater number of cycles than would typically cause dose-limiting toxicity in a patient to whom a second active ingredient is not also being administered.

In another aspect, a compound provided herein is administered daily and continuously for three or four weeks at a dose of from about 0.1 mg to about 1000 mg per day, followed by a rest of one or two weeks. In other embodiments, the dose can be from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In another aspect, a compound provided herein and a second active ingredient are administered orally or parenterally, with administration of the compound provided herein occurring prior to (e.g., about 30 to 60 minutes) the second active ingredient, during a cycle of four to six weeks. In certain embodiments, the compound and second active agent are administered as a single dosage or they are administered separately. In another aspect, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about three to about four cycles.

Combination Therapy

A compound provided herein, or a pharmaceutically acceptable salt thereof, can be combined with other pharmacologically active compounds ("second active agents") in methods and compositions provided herein. Certain combinations may work synergistically in the treatment of particular types of diseases or disorders, and conditions and symptoms associated with such diseases or disorders. A compound provided herein, or a pharmaceutically acceptable salt thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

IV. Pharmaceutical Compositions

The invention provides pharmaceutical compositions comprising a deuterium-enriched compound described herein and a pharmaceutically acceptable carrier. In certain embodiments, the pharmaceutical compositions comprise a therapeutically-effective amount of a deuterium-enriched compound described herein, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Pharmaceutical compositions can be used in the preparation of individual, single unit dosage forms. Pharmaceutical compositions and dosage forms provided herein comprise a compound provided herein, or a pharmaceutically acceptable salt thereof. Pharmaceutical compositions and dosage forms can further comprise one or more excipients. Additionally, pharmaceutical compositions and dosage forms provided herein can comprise one or more additional active ingredients. Examples of optional second, or additional, active ingredients are described above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., Remington's Pharmaceutical Sciences, $18^{th}$ Ed., Mack Publishing, Easton Pa. (1990).

The suitability of a particular excipient may depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient. Lactose-free compositions can comprise excipients that are well known in the art and are listed, for example, in the U. S. Pharmacopeia (USP) 25-NF20 (2002). In general, lactose-free compositions comprise active ingredients, a binder/filler, and a lubricant in pharmaceutically compatible and pharmaceutically acceptable amounts. In another aspect, lactose-free dosage forms comprise active ingredients, microcrystalline cellulose, pre-gelatinized starch, and magnesium stearate.

Also provided are anhydrous pharmaceutical compositions and dosage forms comprising active ingredients. Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are, in another aspect, packaged using materials known to prevent exposure to water such that they can be included in suitable formulary kits. Examples of suitable packaging include, but are not limited to, hermetically sealed foils, plastics, dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In another aspect, dosage forms comprise a compound provided herein in an amount of from about 0.10 to about 500 mg. Examples of dosages include, but are not limited to, 0.1, 1, 2, 5, 7.5, 10, 12.5, 15, 17.5, 20, 25, 50, 100, 150, 200, 250, 300, 350, 400, 450, or 500 mg.

In another aspect, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated, and the amount(s) of a compound provided herein, and any optional additional active agents concurrently administered to the patient.

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18$^{th}$ Ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In another aspect, the invention provides oral dosage forms that are tablets or capsules, in which case solid excipients are employed. In another aspect, the tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in another aspect, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In another aspect, pharmaceutical compositions comprise from about 0.5 to about 15 weight percent of disintegrant, or from about 1 to about 5 weight percent of disintegrant. Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a Syloid® silica gel (AEROSIL200, manufactured by W. R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In another aspect, the invention provides a solid oral dosage form comprising a compound provided herein, anhydrous lactose, microcrystalline cellulose, polyvinylpyrrolidone, stearic acid, colloidal anhydrous silica, and gelatin.

Active ingredients provided herein can also be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719, 5,674,533, 5,059,595, 5,591,767, 5,120,548, 5,073,543, 5,639,476, 5,354,556, and 5,733,566, each of which is incorporated in its entirety herein by reference. Such dosage forms can be used to provide slow or controlled-release of one or more active ingredients using, for example, hydroxypropyl methyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In another aspect, the invention provides single unit dosage forms suitable for oral administration such as, but not limited to, tablets, capsules, gel caps, and caplets that are adapted for controlled-release.

Parenteral dosage forms can be administered to patients by various routes including, but not limited to, subcutaneous, intravenous (including bolus injection), intramuscular, and intraarterial. Administration of a parenteral dosage form bypasses a patient's natural defenses against contaminants, and thus, in these aspects, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated in its entirety herein by reference.

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16th and $18^{th}$ Eds., Mack Publishing, Easton Pa. (1980 & 1990); and Introduction to Pharmaceutical Dosage Forms, $4^{th}$ Ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In another aspect, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are nontoxic and pharmaceutically acceptable. Moisturizers or humectants can also be added to pharmaceutical compositions and dosage forms. Examples of additional ingredients are well known in the art. See, e.g., Remington's Pharmaceutical Sciences, $16^{th}$, and $18^{th}$, Eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other aspects, stearates can serve as a lipid vehicle for the formulation, as an emulsifying agent or surfactant, or as a delivery-enhancing or penetration-enhancing agent. In other aspects, salts of the active ingredients can be used to further adjust the properties of the resulting composition.

In another aspect, the active ingredients provided herein are not administered to a patient at the same time or by the same route of administration. In another aspect, provided are kits which can simplify the administration of appropriate amounts of active ingredients.

In another aspect, the invention provides a kit comprising a dosage form of a compound provided herein. Kits can further comprise additional active ingredients or a pharmacologically active mutant or derivative thereof, or a combination thereof. Examples of the additional active ingredients include, but are not limited to, those disclosed herein.

In other aspects, the kits can further comprise devices that are used to administer the active ingredients. Examples of such devices include, but are not limited to, syringes, drip bags, patches, and inhalers.

V. Definitions

To facilitate an understanding of the present invention, a number of terms and phrases are defined below.

The term "compound" refers to a quantity of molecules that is sufficient to be weighed, tested for its structural identity, and to have a demonstrable use (e.g., a quantity that can be shown to be active in an assay, an in vitro test, or in vivo test, or a quantity that can be administered to a patient and provide a therapeutic benefit).

Unless indicated otherwise, when a D is specifically recited at a position or is shown in a formula, this D represents a mixture of hydrogen and deuterium where the amount of deuterium is about 100% (i.e., the abundance of deuterium ranges from greater than 90% up to 100%). In certain embodiments, the abundance of deuterium in D is from 95% to 100%, or from 97% to 100%.

The term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

"Therapeutically effective amount" includes an amount of a compound of the invention that is effective when administered alone or in combination to treat the desired condition or disorder. "Therapeutically effective amount" includes an amount of the combination of compounds claimed that is effective to treat the desired condition or disorder. The combination of compounds can be additive and is preferably a synergistic combination. Synergy, as described, for example, by Chou and Talalay, Adv. Enzyme Regul. 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower incidence of adverse side effects and/or toxicity, increased efficacy, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, bisulfonic, carbonic, citric, edetic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauric, lauryl sulfonic, maleic, malic, mandelic, methanesulfonic, napsylic, naphthylic, nitric, oleic, oxalic, palmitic, pamoic, pantothenic, phenylacetic, phosphoric, polygalacturonic, propionic, salicylic, stearic, succinic, sulfamic, sulfanilic, sulfuric, tannic, tartaric, toluenesulfonic, and valeric. (See, for example, Berge et al. (1977) "Pharmaceutical Salts", *J. Pharm. Sci.* 66:1-19.). In certain embodiments, the pharmaceutically acceptable salt is a hydrochloric acid salt. In certain other embodiments, the pharmaceutically acceptable salt is a hydrobromic acid salt.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15$^{th}$ Ed., Mack Publ. Co., Easton, Pa. (1975).

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" refers to a diradical of an alkyl group. Exemplary alkylene groups include —$CH_2$—, —$CH_2CH_2$—, and —$CH_2C(H)(CH_3)CH_2$—.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl.

The term "haloalkyl" refers to an alkyl group that is substituted with at least one halogen. Exemplary haloalkyl groups include —$CH_2F$, —$CHF_2$, —$CF_3$, —$CH_2CF_3$, —$CF_2CF_3$, and the like.

The term "hydroxyalkyl" refers to an alkyl group that is substituted with at least one hydroxyl. Exemplary hydroxyalkyl groups include —$CH_2CH_2OH$, —$C(H)(OH)CH_3$, —$CH_2C(H)(OH)CH_2CH_2OH$, and the like.

The term "aralkyl" refers to an alkyl group substituted with an aryl group. Exemplary aralkyl groups include

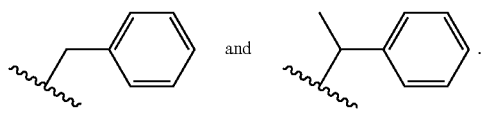

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic aromatic ring systems having two or more carbocyclic rings in which two or more carbons are common to two adjoining rings (the rings are "fused rings") wherein all of the fused rings are aromatic rings, e.g., in a naphthyl group.

The term "heteroaryl" is art-recognized and refers to aromatic groups that include at least one ring heteroatom. In certain instances, a heteroaryl group contains 1, 2, 3, or 4 ring heteroatoms (e.g., O, N, and S). Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic aromatic ring systems having two or more rings in which two or more ring atoms are common to two adjoining rings (the rings are "fused rings") wherein all of the fused rings are heteroaromatic, e.g., in a naphthyridinyl group. In certain embodiments, the heteroaryl is a 5-6 membered monocylic ring or a 9-10 membered bicyclic ring.

The terms ortho, meta, and para are art-recognized and refer to 1,2-, 1,3- and 1,4-disubstituted benzenes, respectively. For example, the names 1,2-dimethylbenzene and ortho-dimethylbenzene are synonymous.

As used herein, the terms "heterocyclic" and "heterocyclyl" represent, for example, an aromatic or nonaromatic ring (e.g., a monocyclic or bicyclic ring) containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include, but are not limited to, pyridine, pyrimidine, indole, purine, quinoline and isoquinoline. Nonlimiting examples of nonaromatic heterocyclic compounds include, but are not limited to, piperidine, piperazine, morpholine, pyrrolidine and pyrazolidine. Examples of oxygen containing heterocyclic rings include, but are not limited to, furan, oxirane, 2H-pyran, 4H-pyran, 2H-chromene, benzofuran, and 2,3-dihydrobenzo[b][1,4]dioxine. Examples of sulfur-containing heterocyclic rings include, but are not limited to, thiophene, benzothiophene, and parathiazine. Examples of nitrogen containing rings include, but are not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the heterocyclyl group is a 3-7 membered ring that, unless specified otherwise, is substituted or unsubstituted.

The term "heterocycloalkyl" refers to a saturated heterocyclyl group having, for example, 3-7 ring atoms (e.g., O, N, or S).

The terms "amine" and "amino" are art-recognized and refer to both unsubstituted and substituted amines, e.g., a moiety that may be represented by the general formulas:

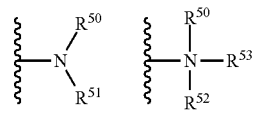

wherein $R^{50}$, $R^{51}$, $R^{52}$ and $R^{53}$ each independently represent a hydrogen, an alkyl, an alkenyl, —(CH$_2$)$_m$—$R^{61}$, or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one of $R^{50}$ or $R^{51}$ may be a carbonyl, e.g., $R^{50}$, $R^{51}$ and the nitrogen together do not form an imide. In other embodiments, $R^{50}$ and $R^{51}$ (and optionally $R^{52}$) each independently represent a hydrogen, an alkyl, an alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and —O—(CH$_2$)$_m$—$R^{61}$, where m and $R^{61}$ are described above.

The term "oxo" is art-recognized and refers to a "=O" substituent. For example, a cyclopentane substituted with an oxo group is cyclopentanone.

The term "S-sulfonamido" refers to a —SO$_2$N($R^A$)($R^B$) group in which $R^A$ and $R^B$ can be independently hydrogen, alkyl, alkenyl, alkynyl, cycloalkyl, cycloalkenyl, cycloalkynyl, aryl, heteroaryl, heterocycloalkyl, aralkyl, or (heterocycloalkyl)alkyl. An S-sulfonamido may be substituted or unsubstituted.

The term "N-sulfonamido" refers to a $R^B$SO$_2$N($R^A$)— group in which $R^A$ and $R^B$ can be independently hydrogen, alkyl, alkenyl, alkynyl, cycloalkyl, cycloalkenyl, cycloalkynyl, aryl, heteroaryl, heterocycloalkyl, aralkyl, or (heterocycloalkyl)alkyl. An N-sulfonamido may be substituted or unsubstituted.

The term "O-carbamyl" refers to a —OC(O)N(R$^A$)(R$^B$) group in which R$^A$ and R$^B$ can be independently hydrogen, alkyl, alkenyl, alkynyl, cycloalkyl, cycloalkenyl, cycloalkynyl, aryl, heteroaryl, heterocycloalkyl, aralkyl, or (heterocycloalkyl)alkyl. An O-carbamyl may be substituted or unsubstituted.

The term "N-carbamyl" refers to a R$^B$OC(O)N(R$^A$)— group in which R$^A$ and R$^B$ can be independently hydrogen, alkyl, alkenyl, alkynyl, cycloalkyl, cycloalkenyl, cycloalkynyl, aryl, heteroaryl, heterocycloalkyl, aralkyl, or (heterocycloalkyl)alkyl. An N-carbamyl may be substituted or unsubstituted.

The term "O-thiocarbamyl" refers to a —OC(S)N(R$^A$)(R$^B$) group in which R$^A$ and R$^B$ can be independently hydrogen, alkyl, alkenyl, alkynyl, cycloalkyl, cycloalkenyl, cycloalkynyl, aryl, heteroaryl, heterocycloalkyl, aralkyl, or (heterocycloalkyl)alkyl. An O-thiocarbamyl may be substituted or unsubstituted.

The term "N-thiocarbamyl" refers to a R$^B$OC(S)N(R$^A$)— group in which R$^A$ and R$^B$ can be independently hydrogen, alkyl, alkenyl, alkynyl, cycloalkyl, cycloalkenyl, cycloalkynyl, aryl, heteroaryl, heterocycloalkyl, aralkyl, or (heterocycloalkyl)alkyl. An N-thiocarbamyl may be substituted or unsubstituted.

The term "C-amido" refers to a —C(O)N(R$^A$)(R$^B$) group in which R$^A$ and R$^B$ can be independently hydrogen, alkyl, alkenyl, alkynyl, cycloalkyl, cycloalkenyl, cycloalkynyl, aryl, heteroaryl, heterocycloalkyl, aralkyl, or (heterocycloalkyl)alkyl. A C-amido may be substituted or unsubstituted.

The term "N-amido" refers to a R$^B$C(O)N(R$^A$)— group in which R$^A$ and R$^B$ can be independently hydrogen, alkyl, alkenyl, alkynyl, cycloalkyl, cycloalkenyl, cycloalkynyl, aryl, heteroaryl, heterocycloalkyl, aralkyl, or (heterocycloalkyl)alkyl. An N-amido may be substituted or unsubstituted.

The symbol " $\sim\!\sim$ " indicates a point of attachment.

The term "substituted" means that one or more hydrogens on the atoms of the designated group are replaced with a selection from the indicated group, provided that the atoms' normal valencies under the existing circumstances are not exceeded, and that the substitution results in a stable compound. Combinations of substituents and/or variables are permissible only if such combinations result in stable compounds. The terms "stable compound' or "stable structure" refer to a compound that is sufficiently robust to survive isolation to a useful degree of purity from a reaction mixture, and formulation into an efficacious therapeutic agent.

When any substituent or variable occurs more than one time in any constituent or the compound of the invention, its definition on each occurrence is independent of its definition at every other occurrence, unless otherwise indicated.

It should also be noted that any carbon as well as heteroatom with unsatisfied valences in the text, schemes, examples and tables herein is assumed to have the sufficient number of hydrogen atom(s) to satisfy the valences.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, if a variable is not accompanied by a definition, then the previous definition of the variable controls.

The terms "a" and "an" as used herein mean "one or more" and include the plural unless the context is inappropriate.

Finally, the invention may be embodied in other specific forms without departing from the spirit or essential attributes thereof. This invention encompasses all combinations of aspects and embodiments of the invention noted herein. It is understood that any and all aspects of the invention may be taken in conjunction with any other aspects and/or embodiments to describe additional aspects. It is also to be understood that each individual element of the aspects is intended to be taken individually as its own independent aspect. Furthermore, any element of an aspect is meant to be combined with any and all other elements from any aspect to describe an additional aspect.

INCORPORATION BY REFERENCE

All references listed herein are individually incorporated in their entirety by reference.

EQUIVALENTS

Numerous modifications and variations of the invention are possible in light of the above teachings. It is therefore to be understood that within the scope of the appended claims, the invention may be practiced otherwise that as specifically described herein.

The invention claimed is:

1. A compound of Formula II

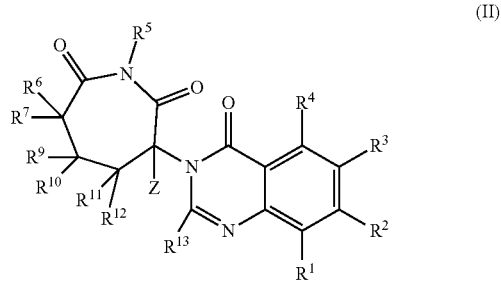

or a pharmaceutically acceptable salt, solvate, or stereoisomer thereof, wherein:

Z is H or D, provided that the abundance of deuterium in Z is at least 30%;

R$^5$, R$^6$, R$^7$, R$^9$, R$^{10}$, R$^{11}$, and R$^{12}$ are each independently selected from H and D;

R$^{13}$ is selected from: H; D; halo, —(CH$_2$)$_n$OH, phenyl, —O(C$_1$-C$_6$)alkyl, and (C$_1$-C$_6$)alkyl optionally substituted with one or more halo;

R$^1$, R$^2$, R$^3$, R$^4$ are each independently selected from: H, D, halo, hydroxyl, —NR$^b$R$^c$, —(CH$_2$)$_n$OH, (C$_1$-C$_6$) alkyl optionally substituted with one or more halo, (C$_1$-C$_6$)alkoxy optionally substituted with one or more halo, —(CH$_2$)$_n$NHR$^a$, R$^{14a}$, R$^{14b}$, and R$^{14c}$;

alternatively, two of R$^1$, R$^2$, R$^3$, and R$^4$ are taken together with the atoms to which they are attached to form a 5-6 membered carbocyclic or heterocyclic ring optionally substituted with one or more groups independently selected from halo, (C$_1$-C$_6$)alkyl optionally substituted with one or more halo, and (C$_1$-C$_6$)alkoxy optionally substituted with one or more halo R$^a$ is selected from: H, D, (C$_1$-C$_6$)alkyl optionally substituted with one or more halo, —(CH$_2$)$_n$-(6 to 10 membered aryl), —C(O)(CH$_2$)$_n$-(6 to 10 membered aryl), —C(O)(CH$_2$)$_n$-(6 to 10 membered heteroaryl), —C(O)(C$_1$-C$_8$)alkyl optionally substituted with one or more halo, —C(O)(CH$_2$)$_n$—(C$_3$-C$_{10}$-cycloalkyl), —C(O)(CH$_2$)$_n$—NR$^b$R$^c$, —C(O)(CH$_2$)$_n$—O-(C$_1$-C$_6$)alkyl, and —C(O)(CH$_2$)$_n$—O—(CH$_2$)$_n$-(6 to 10 membered aryl); wherein the aryl and heteroaryl are optionally substituted with one or more groups selected from: halo, —SCF$_3$, (C$_1$-C$_6$)alkyl optionally substituted with one or more halo, and (C$_1$-C$_6$)alkoxy optionally substituted with one or more halo;

R$^b$ and R$^c$ are each independently selected from: H, D, (C$_1$-C$_6$)alkyl optionally substituted with one or more halo, (C$_1$-C$_6$)alkoxy optionally substituted with one or more halo, and 6 to 10 membered aryl; wherein the aryl is optionally substituted with one or more groups selected from: halo, (C$_1$-C$_6$)alkyl optionally substituted with one or more halo, and (C$_1$-C$_6$)alkoxy optionally substituted with one or more halo;

R$^{14a}$ is selected from: H, D, halo, —(CH$_2$)$_n$OH, (C$_1$-C$_6$) alkyl optionally substituted with one or more halo, and (C$_1$-C$_6$)alkoxy optionally substituted with one or more halo;

R$^{14b}$=—(CH$_2$)$_n$—NHR$^d$;

R$^{14c}$=—(CH$_2$)$_n$—NHR$^x$;

R$^d$ is selected from: H, D, —(C$_1$-C$_6$)alkyl optionally substituted with one or more halo, —C(O)(C$_1$-C$_8$)alkyl optionally substituted with one or more halo, —C(O)(CH$_2$)$_n$(C$_3$-C$_{10}$-cycloalkyl), —C(O)(CH$_2$)$_n$NR$^e$R$^f$, and —C(O)(CH$_2$)$_n$O(C$_1$-C$_6$)alkyl;

R$^e$ and R$^f$ are each independently selected from: hydrogen; (C$_1$-C$_6$)alkyl optionally substituted with one or more halo; and (C$_1$-C$_6$)alkoxy optionally substituted with one or more halo;

R$^x$ is selected from: —C(O)(CH$_2$)$_n$NHR$^h$; —(CH$_2$)$_n$-(6 to 10 membered aryl); —C(O)(CH$_2$)$_n$-(6 to 10 membered aryl); —C(O)(CH$_2$)$_n$-(6 to 10 membered heteroaryl); and, —C(O)(CH$_2$)$_n$O(CH$_2$)$_n$-(6 to 10 membered aryl), wherein the aryl and heteroaryl are optionally substituted with one or more groups selected from: halo; —SCF$_3$; (C$_1$-C$_6$)alkyl optionally substituted with one or more halo; and, (C$_1$-C$_6$)alkoxy substituted with one or more halo;

R$^h$ is selected from: 6 to 10 membered aryl optionally substituted with one or more groups selected from: halo; (C$_1$-C$_6$)alkyl optionally substituted with one or more halo; and, (C$_1$-C$_6$)alkoxy optionally substituted with one or more halo;

n is independently selected from selected from 0, 1, and 2; and a hydrogen atom present in any substituent is optionally replaced by D.

2. The compound of claim 1, wherein the compound is a compound of Formula II-Y represented by:

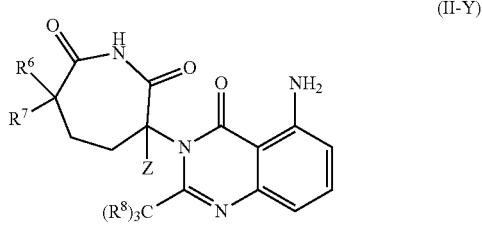

(II-Y)

or a pharmaceutically acceptable salt, solvate, or stereoisomer thereof; wherein Z is H or D, provided that the abundance of deuterium in Z is at least 30%; R$^6$, R$^7$, and R$^8$ are independently H or D; and any hydrogen atom may be optionally replaced with D.

3. The compound of claim 1, wherein the compound is a compound of Formula II-B represented by:

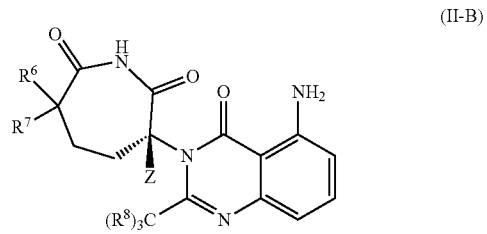

(II-B)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and R$^6$, R$^7$, and R$^8$ are independently H or D.

4. The compound of claim 1, wherein the compound is a compound of Formula II-C represented by:

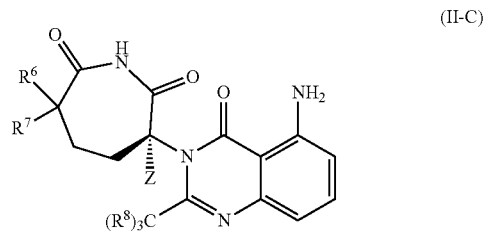

(II-C)

or a pharmaceutically acceptable salt or solvate thereof; wherein the compound has a stereochemical purity of at least 75% enantiomeric excess at the carbon atom bearing variable Z; Z is H or D, provided that the abundance of deuterium in Z is at least 30%; and R$^6$, R$^7$, and R$^8$ are independently H or D.

5. The compound of claim 1, wherein the compound is a compound of Formula II-H represented by:

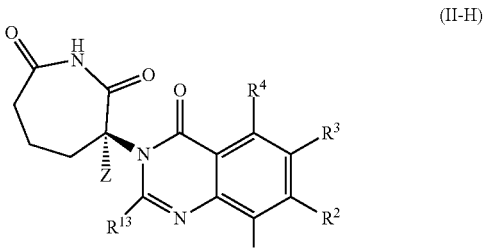

(II-H)

or a pharmaceutically acceptable salt or solvate thereof; wherein the compound has a stereochemical purity of at least 75% enantiomeric excess at the carbon atom bearing variable Z; and R$^{13}$ is CH$_3$ or CD$_3$.

6. The compound of claim 1, wherein the compound is a compound of Formula II-J represented by:

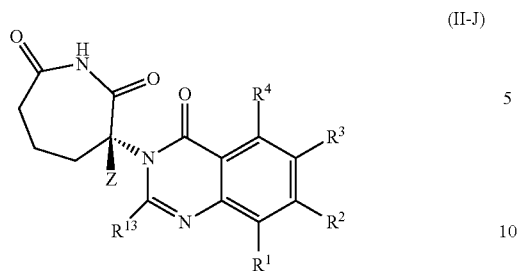
(II-J)
or a pharmaceutically acceptable salt or solvate thereof; wherein the compound has a stereochemical purity of at least 75% enantiomeric excess at the carbon atom bearing variable Z; and $R^{13}$ is $C_3$ or $CD_3$.
* * * * *